United States Patent
Zhu et al.

(10) Patent No.: US 6,784,343 B2
(45) Date of Patent: Aug. 31, 2004

(54) PROTEINS AND DNA RELATED TO SALT TOLERANCE IN PLANTS

(75) Inventors: Jian-Kang Zhu, Tucson, AZ (US); Jiping Liu, Tucson, AZ (US); Manabu Ishitani, Tucson, AZ (US); Cheol-Soo Kim, Tucson, AZ (US); Ursula Halfter, Tucson, AZ (US)

(73) Assignee: The Arizona Board of Regents, Tucson, AZ (US)

( * ) Notice: Subject to any disclaimer, the term of this patent is extended or adjusted under 35 U.S.C. 154(b) by 101 days.

(21) Appl. No.: 09/824,735

(22) Filed: Apr. 4, 2001

(65) Prior Publication Data

US 2002/0095032 A1 Jul. 18, 2002

Related U.S. Application Data

(60) Provisional application No. 60/194,649, filed on Apr. 4, 2000.

(51) Int. Cl.$^7$ .......................... C12N 15/11; C12N 15/29; C12N 15/87; A01H 5/00
(52) U.S. Cl. ....................... 800/298; 800/278; 800/287; 800/320.3; 800/320.1; 800/314; 800/320; 800/312; 536/23.1; 536/23.6; 435/320.1; 435/468
(58) Field of Search ................................. 800/278, 295, 800/298, 287, 320.1, 314, 320, 312; 536/23.1, 23.6; 435/468, 419, 320.1

(56) References Cited

U.S. PATENT DOCUMENTS 5,451,514 A * 9/1995 Boudet et al. ........... 435/172.3

OTHER PUBLICATIONS

Halfter et al (2000, PNAS 97(7):3735–3740).*
Larkin et al (1994, The Plant Cell 6:1065–1076).*
Bowie et al (1990, Science 247:1306–10).*
McConnell et al (2001, Nature 411 (6838):709–713).*
Liu et al (2000 PNAS 97(7):3730–3734).*
Fourgoux–Nicol et al (1999, Plant Molecular Biology 40:857–872).*

* cited by examiner

Primary Examiner—Phuong T. Bui
Assistant Examiner—Stuart F. Baum
(74) Attorney, Agent, or Firm—Oblon, Spivak, McClelland, Maier & Neustadt, P.C.

(57) ABSTRACT

The present invention relates to proteins and nucleic acids related to salt tolerance in plants.

66 Claims, 9 Drawing Sheets

FIG. 2A

| Kinase | Regulatory Domain |

FIG. 2B

TCGATCAGAT AAAAGTTTGTAAAGA

```
      ATGACAAAGAAAATGAGAAGAGTGGCCAAGTACGACGTTGGTCCCACAATACGTGAACGAACCTTTCCTAACGTTAAG
  1   M  T  K  K  M  R  R  V  G  K  Y  E  V  G  R  T  L  E  I  T  F  A  K  I  K
                                                        -- I --
      TTTCCGACGAACACAGACACTGGTGATAATGTACCCATCAAAATTATGGCTAAGAGTACAATACTTAAGAACAGAATG
 27   F  A  R  N  T  D  T  G  D  N  V  I  I  I  M  A  K  S  T  I  L  K  N  R  M
                                                        -- II --
      GTTGATCAGATAAAAAGAGAGATATCTATAATGAAGATTGTTCGTCACCCGAACATAGTGAGGTTGTATGACGTGTTG
 53   V  D  Q  I  K  R  I  I  S  I  M  K  I  V  R  H  P  N  I  V  R  L  Y  E  V  L
                      -- III --                         -- IV --
      CGCACTCCTTCGAAAATATATATAGTTTTCGAGTTTGTGACAGGACGAGACCTCTTTGATAGAATTGTTCATAAACTG
 79   A  S  P  S  K  I  Y  I  V  L  E  F  V  T  G  G  E  L  F  D  R  I  V  H  K  G
                                                     -- V --
      ACCCTTGAAGAAAGTGAGTCTCGGAAATACTTTCAACACCTTGTAGATGCTGTTGCTCATTGTCACTCCAAGGGTGTT
 105  R  L  E  E  S  E  S  R  K  Y  F  Q  Q  L  V  D  A  V  A  H  C  K  G  V
                                                           -- VI --
      TACCACCGTGACCTAAACCCAGAAAATCTTTTACTCGATACAAATCGAAATCTGAACGTTTCCGATTTCCGACTCAGT
 131  Y  I  R  I  L  K  P  E  I  L  L  D  T  N  G  N  L  K  I  S                L  S
                                                           -- VII --
      CCATTCCCTCACGAACGACTAGAACTTCTCCGTACCACATGTCGAACTCCGAACTATGTACCTCCAGACGTACTTAGT
 157  A  L  P  Q  E  G  V  E  L  L  R  T  T  C  G  I  P  N  V  A  P  I  V  L  S
                                                     -- VIII --
      CGACACGGTTACGATCGTTCACCACCTGATATTTGGTCTTCCCCGGTTATTCTTTTGGTTATATTCCCTCGATATTTA
 183  G  Q  G  Y  D  G  S  A  A  I  I  W  S  C  I  I  L  F  V  I  L  A  G  Y  L
                                                     -- IX --
      CCTTTTTCCGAGACCGATCTTCCACCGTTGTACAGAAAAATAAATCCACCGAGTTTCTTGTCCACCGTCGTTTCC
 209  P  F  S  E  T  D  L  P  G  L  Y  R  K  I  N  A  A  E  F  S  C  P  P  W  F  S
                                                     -- X --
      CCAGAAGTGAAGTTTTTAATACATAGGATACTTGACCCCAATCCCAAAACACGTATTCAAATTCAACGAATCAAGAAA
 235  A  E  V  K  F  L  I  H  R  L  D  P  N  P  K  T  R  I  Q  I  Q  G  I  K  K
                                                     -- XI --
      GATCCTTTCGTTCAGATTAAATTATGTCCCTATACGAGCAACCGAACAAGAAGAAGTGAATTTCGATGATATTCGTCCA
 261  D  P  W  F  R  L  N  Y  V  P  I  R  A  R  E  E  E  E  V  N  L  D  D  I  R  A
      GTTTTTGATGGAATTGACCCCCAGTTATGTACCCGAGAATGTAGAGACAAATGATGAACGCCCCCTGATGATGAATCCC
 287  V  F  D  G  I  E  G  S  Y  V  A  E  N  V  E  R  N  D  E  G  P  L  M  M  N  A
      TTTGACATGATTACCTTATCACAACCCTTAAATTTATCTCCACTATTTGACAGGCGACAGGATTTTGTTAAACCCAA
 313  F  E  M  I  T  L  S  Q  G  L  N  L  S  A  L  F  D  R  R  Q  D  F  V  K  R  Q
      ACCCGTTTTGTTTCTCGAAGCGAACCTAGTGAGATAATTCCTAACATTGACCCTGTACCGAACTCAATGGGTTTTAAG
 339  T  R  F  V  S  R  R  E  P  S  E  I  I  A  N  I  E  A  V  A  N  S  M  G  F  K
      TCTCATACACGAAACTTCAAGACAAGCCTCGACCGATTATCTTCGATCAACGCCCGACAGTTACCTGTTGTGATAGAG
 365  S  H  T  R  N  F  K  T  R  L  E  G  L  S  S  I  K  A  G  Q  L  A  V  V  I  E
      ATTTACGAGGTTGCCACCATGCCTTTTCATGGTAGACGTAAGAAACCCTCCTGGTGAAACTCTTGAATATCACAAGTTC
 391  I  Y  E  V  A  P  S  L  F  M  V  D  V  R  K  A  A  G  E  T  L  E  Y  H  K  F
      TACAAGAACCTATGTTCGAAACTGGAAAACATAATATCGACCCCAACAGAACGAATACCAAAGTCAGAGATTCTCAGA
 417  Y  K  K  L  C  S  K  L  E  N  I  I  W  R  A  T  E  G  I  P  K  S  E  I  L  R
      ACAATCACCTTTTTGATCCCAACTTAA
 437  T  I  T  F
```

TGGATCAGATAAAAGTTTGTAAAGA
ATGACAAAGAAAATGAGAAGAGTGGGCAAGTACGAGGTTGGTCGCACAATAGGTGAAGGAACCTTTGCTAAGGTTAAG
1  M  T  K  K  M  R  R  V  G  K  Y  E  V  G  R  T  E  G  T  F  A  K  V  K
                                                   -- I --

TTTGCGGAGGAACACAGACACTGGTGATAATGTAGCCATCAAAATTATGGCTAAGAGTACAATACTTAAGAACAGAATG
27 F  A  R  N  T  D  T  G  D  N  V  A  I  K  I  M  A  K  S  T  I  L  K  N  R  M
                                        -- II --

GTTGATCAGATAAAAGAGAGATATCTATAATGAAGATTGTTCGTCACCCGAACATAGTGAGGTTGTATGAGGTGTTG
53 V  D  Q  I  K  R  E  I  S  I  M  K  I  V  R  H  P  N  I  V  R  L  Y  E  V  L
                     -- III --                            -- IV --

GCGAGTCCTTCGAAAATATATATAGTTTGTTGGAGTTTGTTGACAGGAGAGCTCTTTGATAGAATTGTTCATAAAGGG
79 A  S  P  S  K  I  Y  I  V  L  E  F  V  T  G  G  E  L  F  D  R  I  V  H  K  G
                                              -- V --

AGGCTTGAAGAATCTTCGAGGAAGTATTTACTCGATACAAATGGAAATCGAAGGTTTCGGATTCGGACTCAGT
105 R  L  E  E  S  S  R  K  Y  F  Q  Q  L  V  D  A  V  A  H  C  K  G  V
                                                       -- VI --

TACCACGTGACCTAAAGCCAGAAAATCTTTTACTCGATACAAATGGAAATCGAAGGTTTCGGATTCGGACTCAGT
131 Y  H  R  D  L  K  P  E  N  L  L  L  D  T  N  G  N  L  K  V  S  D  F  G  L  S
     -- VII --

GCATTGCCTCAGGAGGAGTAGAACTTCTGCGTACCACATGTGGAACTCCGAACTATGTAGCTCCAGAGGTACTTAGT
157 A  L  P  Q  E  G  V  E  L  R  T  T  C  G  P  N  Y  V  A  P  E  V  L  S
                                         -- VIII --

FIG. 2B(1)

```
     GGACAGGGTTACGATGGTTCAGCAGCTGATATTGGTCTTTGCGGGGTTATTCTTTTCGTTATATTGGCTGGATATTTA
183  G  Q  G  Y  D  G  S  A  A  D  I  W  S  C  G  V  I  L  F  V  I  L  A  G  Y  L
                                          -- IX --

CCTTTTTCCGAGACGGATCTTCCAGGGTTGTACAGAAAAATAAATGCAGAGAGTTTTCTTGTCATGTCCACCGTGGTTTCC
209  P  F  S  E  T  D  L  P  G  L  Y  R  K  I  N  A  A  E  F  S  C  P  P  W  F  S
                                                   -- X --

GCAGAAGTTGAAGTTTTTAATACATAGGATACTTGACCCCAATCCCAAAACACGTATTCAAATTCAAGGAATCAAGAAA
235  A  E  V  K  F  L  I  H  R  I  L  D  P  N  P  K  T  R  I  Q  Q  G  I  K  K
                         -- XI --

GATCCTTGGTTCAGATTAAAATTATGTGCCTATACGAGCAAGGAAGAAGAAGAAGTGAATTTGGATGATATTCGTGCA
261  D  P  W  F  R  L  N  Y  V  P  I  R  A  R  E  E  E  E  V  N  L  D  D  I  R  A

GTTTTTGATGGAATTGAGGGCAGTTATGTAGCGGAGAATGTAGAGAGAAATGATGAAGGCCCCTGATGATGAATGCC
287  V  F  D  G  I  E  G  S  Y  V  A  E  N  V  E  R  N  D  E  G  P  L  M  M  N  A

TTTGAGATGATTACCTTATCACAAGGCTTAAATTTATCTGCACTATTTGACAGGCGACAGGATTTTGTTAAAAGGCAA
313  F  E  M  I  T  L  S  Q  G  L  N  L  S  A  L  F  D  R  R  Q  D  F  V  K  R  Q

ACCCGTTTTGTTTCTCGAAGGGAACCTAGTGAGATAATTGCTAACATTGAGGCTGTAGCGAACTCAATGGGTTTAAG
339  T  R  F  V  S  R  R  E  P  S  E  I  I  A  N  I  E  A  V  A  N  S  M  G  F  K
```

FIG. 2B(2)

365 TCTCATATACACGAAACTTCAAGAGACAAGGCTCGAGGGATTATCTTCGATCAAGGCCGACAGTTAGCTGTTGTGATAGAG
    S  H  T  R  N  F  K  T  R  L  E  G  L  S  S  I  K  A  G  Q  L  A  V  V  I  E

391 ATTACGAGGTGGCACCATCGCTTTTCATGGTAGACGTAAGAAAGGCTGTGGTGAAACTCTTGAATATCACAAGTTC
    I  Y  E  V  A  P  S  L  F  M  V  D  V  R  K  A  A  G  E  T  L  E  Y  H  K  F

417 TACAAGAAGCTATGTTCGAAACTGGAAAACATAATATGGAGGGCAACAGAAGGAATACCAAAGTCAGAGATTCTCAGA
    Y  K  K  L  C  S  K  L  E  N  I  I  W  R  A  T  E  G  I  P  K  S  E  I  L  R

437 ACAATCACGTTTTGATCCCAACTTAA
    T  I  T  F

*FIG. 2B(3)*

```
                                                                          *
SOS2    1                        MTKKMRRVGKYEVGRTIGEGTFAKVKFARNEDTGEDVAIKIMAKSTILKNRMVDQ
AMPK    1   MAEKQKHDGRVKIGHYMLGDTLGMGTFGKVKIG-HDLTG-HKVAVKILNRQKIRSLDVVGK
SNF1   45   SLADGAHIGNYRIVKTLGEGSFGKVKLAYHTTTGQKVALKIINKKVLAKSDMQGR

SOS2   56   IKREISIMKIVRHPNIVRLYEVLASPSKIYIVLEFVTGGELFDRIVHKGRLEEDESRKYF
AMPK   61   IQNLKLFRHPHIIKLYQVISTPTDFFMVMEYVSGGELFDYICKHGRVEEMEARRLF
SNF1  101   EREISYMLRLLRHPHIIKLYDVIKSKDEIIMVIEYA-GNELFDYIVQRDKMSEDEARRFF

SOS2  116   QQLVDAVAHCHCKGVYHRDLKPENLLLDTNGNLKVSDFGLSALPQEGVELRTTCGTPNY
AMPK  121   QQILSAVDYCHRMVVHRDLKPENVLLDAHMNVKIADFGLSNMMSDG-EFLRTSCGSPNY
SNF1  161   QQIISAVEYCHRHKIVHRDLKPENLLLDEHLNVKIADFGLSNIMTDG-NFLKTSCGSPNY

SOS2  176   VAPEVLSGKGYDGAAADIWSCGVILFVILAGYLPFSETDLPGLYRKINAAEFSCPPWFSA
AMPK  180   TAPEVISGRLYAGPEVDIWSCGVILYALLCGTLPFDDEHVPTLFKKIRGGVFYIPEYLNR
SNF1  221   AAPEVISGKLYAGPEVDVWSCGVILYVMLCRRLPFDDESIPVLFKNISNGVYTLPKELSP

SOS2  236   EMKFLIHRILDPNPKTRITIQQIKQHPMFRLN
AMPK  240   SVATLMHMLQVDPLKRATIKDIREHEWFKQG
SNF1  282   GAAGLIKRMLIVNPLNRISIHEIMQDDWFKVD
```

FIG. 3A

```
SDS2 332  QDFVKRQTRFMSRREPSE AN EAVANSMGFKS---  HTRNFKTRLEG SS I AGQ AVW
CHK1 389  ICPPERLTRFYSRASRET  DH MDS RL A ISVTMKYVRN TI MN DKRKCL QGV
CHK1 371  QRLVKRMTRFFTKL DA DKSYQC KE CEKLG YQW--- KSCMNQ T ST DRRNNK IFK

SDS2 389  IE YEVAPS L FMVDVRKAAGE IL EYHKFYKK  SKLEN  WRATEG P
CHK1 449  IE TN HN ELINE IKRN  PLEWRKFFK MV SS IGKP VL TD M SQN
CHK1 428  MN EMD-DK IL VDFR LSK GD EFKR EL KGK I D V SSQK M L P
```

*FIG. 3B*

SEQUENCE LISTING

<160> NUMBER OF SEQ ID NOS: 16

<210> SEQ ID NO 1
<211> LENGTH: 5144
<212> TYPE: DNA

<213> ORGANISM: Arabidopsis thaliana
<220> FEATURE:
<221> NAME/KEY: CDS
<222> LOCATION: (2004)..(2168)
<223> OTHER INFORMATION:
<221> NAME/KEY: CDS
<222> LOCATION: (2255)..(2317)
<223> OTHER INFORMATION:
<221> NAME/KEY: CDS
<222> LOCATION: (2416)..(2487)
<223> OTHER INFORMATION:
<221> NAME/KEY: CDS
<222> LOCATION: (2573)..(2680)
<223> OTHER INFORMATION:
<221> NAME/KEY: CDS
<222> LOCATION: (2778)..(2852)
<223> OTHER INFORMATION:
<221> NAME/KEY: CDS
<222> LOCATION: (2921)..(3100)
<223> OTHER INFORMATION:
<221> NAME/KEY: CDS
<222> LOCATION: (3225)..(3314)
<223> OTHER INFORMATION:
<221> NAME/KEY: CDS
<222> LOCATION: (3418)..(3540)
<223> OTHER INFORMATION:
<221> NAME/KEY: CDS
<222> LOCATION: (4052)..(4171)
<223> OTHER INFORMATION:
<221> NAME/KEY: CDS
<222> LOCATION: (4400)..(4516)
<223> OTHER INFORMATION:
<221> NAME/KEY: CDS
<222> LOCATION: (4735)..(4791)
<223> OTHER INFORMATION:
<221> NAME/KEY: CDS
<222> LOCATION: (4879)..(4953)
<223> OTHER INFORMATION:
<221> NAME/KEY: CDS
<222> LOCATION: (5038)..(5130)
<223> OTHER INFORMATION:

<400> SEQUENCE: 1

```
tttttggcgg gaaatctcg ggtttacgtt tttggcggga aaatctcgtg tttacgtttt      60
tggcgggaaa atctcgggtt tacgtttttt gcgagaaaat cacgggttta cttttttttg    120
cgggaaaatc acggatttat gttttttggt ggaaaaatta cgagtttact ttttctcaat    180
ttcattgctt gtatatttaa gaaatttgga aaaatattaa ttttattaaa ttggtttaga    240
tgtgttggtt aaacctaaat tggcattggt ttagagattt tagttggttt tattcaattt    300
tacaaaattt gatgggttaa ttggataaac catggaaacc attaaccatt acaacctaac    360
tcattttact catcaaacca attgactcat caactcattt gactcatcaa ctcatttgag    420
tcaaaaattt caactcatta gggttcatgg gttgagttga gttgagttga cccatgaatt    480
ttgacccatt ttgacacccc tacatatgat cataagttaa taatcaaaaa ttactattga    540
taacttttta acggaattgt tttgtaagtt tcatttacgt tatttatata aaaaaacata    600
atgcaaaagt actaatgtat agttattttt atttttaata atgcaaaaat attactgtaa    660
tacttttttca ttcttatcaa tatttttcct tatattcaat tagccaccaa cacctacatt    720
tcatatttct cttcacattc attattttct tgctcttgta ttccttctta tcatcttcat    780
tgccaatttt tcattgacat tgtcatcgtt actttgtatg tatgattttt gaacatttaa    840
tgtgaatccc aaccgactat aggactatca agaagttttc aaacttttta aaaaagatct    900
tgaaccttta aagcaaatcc caaccgacta tagaaccata gtcctcttcc ttgttgatga    960
agctcttctc gtgccggcga aaatctaggc cataaaagcc tcttcaacat cacctagtat   1020
attgaccgtg accatctttt tgaccattgc tttgtgaatg aaccgtcgat aaaccgtgtt   1080
```

-continued

```
atcacttacg ccaaatttttt ccctagtgtt tgtttccaaa ctctcacgaa tccttatcga    1140
acttttttat atatcactt gtagcattgg aaagtatctt tgtatgcttt gtcttaaact      1200
tagacatcct tgttctcttg gttttttttga accttgcttg acttaaatga agttaaaaat    1260
ttgtagttaa aaatagaaaa ttttactaat ttgagttcga ttaatcatag tctagataat    1320
ttgaaaaaaa ttaaaataaa ttttgaaaat actatatgtt tatttttttaa aaataattta   1380 ctaaattgat aagtgatatt agattagttt ttttttttctt tttttaaattt tgaaaacctc  1440 acaattatta aattgaaaga ttcaaaatgc aatgttagtt tttaaaagtt taatcaccca    1500
aacggataat tgacccgaac gactaattca ggtcgtatac gggtacagtc aaataacccg   1560
acccgaaatg ctcaacggat ctgcacggac gttcgcatcg acgattcacg gctttcgcga   1620
atcgcatcac gagccttcct tctctcctac gcctcttttca tcaacccttc tctgcgaatc   1680
caattctggt atttcacgat tctctttcga ctacgcccaa tcgcaattcc agccgtacga    1740
attttatata ttgattatga tcttgatcct tacctttttcg tcgtttcctt gatcgaattt    1800
atgttgattt atgctgcgaa atcaaaatta tggatacaga gtaattttgt atatatggat    1860
gtgtaggagc taaaattagc aaacaatacg taaagtaatt gaaatcgaaa tcataaacgt    1920
ttaaggaaag aggtttttac taagtctctg aataatctga ttgatagctt gtggtcaatg    1980
gatcagataa aagtttgtaa aga atg aca aag aaa atg aga aga gtg ggc aag    2033
                         Met Thr Lys Lys Met Arg Arg Val Gly Lys
                          1               5                  10 tac gag gtt ggt cgc aca ata ggt gaa gga acc ttt gct aag gtt aag       2081
Tyr Glu Val Gly Arg Thr Ile Gly Glu Gly Thr Phe Ala Lys Val Lys
         15                  20                  25 ttt gcg agg aac aca gac act ggt gat aat gta gcc atc aaa att atg       2129
Phe Ala Arg Asn Thr Asp Thr Gly Asp Asn Val Ala Ile Lys Ile Met
     30                  35                  40 gct aag agt aca ata ctt aag aac aga atg gtt gat cag gtatgttctg        2178
Ala Lys Ser Thr Ile Leu Lys Asn Arg Met Val Asp Gln
 45                  50                  55 gattgttttt tacatggaaa ctaaggttgt tgcgtcaatg gtatgatctt tgatttcgtt    2238
taaagctctt ttacag ata aaa aga gag ata tct ata atg aag att gtt cgt   2290
              Ile Lys Arg Glu Ile Ser Ile Met Lys Ile Val Arg
                             60                   65 cac ccg aac ata gtg agg ttg tat gag gtatgtttgt ttgtttccat             2337
His Pro Asn Ile Val Arg Leu Tyr Glu
     70                   75 gcatctgcga aatttttatct ctgaagtgtt tttgcatcat tgttcttctg ttgttttttt    2397
gtgattttcc cgatgtag gtg ttg gcg agt cct tcg aaa ata tat ata gtt       2448
                   Val Leu Ala Ser Pro Ser Lys Ile Tyr Ile Val
                                 80                  85 ttg gag ttt gtg aca gga gga gag ctc ttt gat aga att gtacggaact        2497
Leu Glu Phe Val Thr Gly Gly Glu Leu Phe Asp Arg Ile
         90                  95                 100 tccatacttg taggcagcgt ccattagtta aaacctctct acttaatttt ttaatatatg    2557
aaatctttca tgcag gtt cat aaa ggg agg ctt gaa gaa agt gag tct cgg      2608
            Val His Lys Gly Arg Leu Glu Glu Ser Glu Ser Arg
                              105                 110 aaa tac ttt caa cag ctt gta gat gct gtt gct cat tgt cac tgc aag       2656
Lys Tyr Phe Gln Gln Leu Val Asp Ala Val Ala His Cys His Cys Lys
         115                 120                  125 ggt gtt tac cac cgt gac cta aag gtaaagacgt gtttttgttt accaatattc      2710
Gly Val Tyr His Arg Asp Leu Lys
```

-continued

```
          130                 135
ctcagaatat ctcactgcgt tgcaatccag acttgatatt tttgtgtcgc tatgttatgt        2770 tatctag cca gaa aat ctt tta ctc gat aca aat gga aat ctg aag gtt          2819
        Pro Glu Asn Leu Leu Leu Asp Thr Asn Gly Asn Leu Lys Val
                140                 145                 150 tcg gat ttc gga ctc agt gca ttg cct cag gaa gtaagtgctc ttatctctgc        2872
Ser Asp Phe Gly Leu Ser Ala Leu Pro Gln Glu
                155                 160 ttcagcagtc tgcttacgtg gtcattaact tgttatatac tcaatcag gga gta gaa        2929
                                                     Gly Val Glu ctt ctg cgt acc aca tgt gga act ccg aac tat gta gct cca gag gta          2977
Leu Leu Arg Thr Thr Cys Gly Thr Pro Asn Tyr Val Ala Pro Glu Val
165                 170                 175                 180 ctt agt gga cag ggt tac gat ggt tca gca gct gat att tgg tct tgc          3025
Leu Ser Gly Gln Gly Tyr Asp Gly Ser Ala Ala Asp Ile Trp Ser Cys
                185                 190                 195 ggg gtt att ctt ttc gtt ata ttg gct gga tat tta cct ttt tcc gag        3073
Gly Val Ile Leu Phe Val Ile Leu Ala Gly Tyr Leu Pro Phe Ser Glu
                200                 205                 210 acg gat ctt cca ggg ttg tac aga aaa gtaagtaaca tatctttcgg                3120
Thr Asp Leu Pro Gly Leu Tyr Arg Lys
                215                 220 gaagaaatca tgaattcctt gtcatggctt ttgtcaaacc gtttattgat ttggttttgc        3180
aatttcaccc ttagttttga gcttttacac attgttattt acag ata aat gca gca        3236
                                                Ile Asn Ala Ala
                                                            225 gag ttt tct tgt cca ccg tgg ttt tcc gca gaa gtg aag ttt tta ata          3284
Glu Phe Ser Cys Pro Pro Trp Phe Ser Ala Glu Val Lys Phe Leu Ile
                230                 235                 240 cat agg ata ctt gac ccc aat ccc aaa aca gtgagtattt tgctttgttc            3334
His Arg Ile Leu Asp Pro Asn Pro Lys Thr
                245                 250 tctcctagct atcaggtttt ggtgatattt aatgttctag taattatatc tgtttatcta        3394
ttattgtttc tcaattagag cag cgt att caa att caa gga atc aag aaa gat        3447
                      Arg Ile Gln Ile Gln Gly Ile Lys Lys Asp
                                      255                 260 cct tgg ttc aga tta aat tat gtg cct ata cga gca agg gaa gaa gaa          3495
Pro Trp Phe Arg Leu Asn Tyr Val Pro Ile Arg Ala Arg Glu Glu Glu
                265                 270                 275 gaa gtg aat ttg gat gat att cgt gca gtt ttt gat gga att gag              3540
Glu Val Asn Leu Asp Asp Ile Arg Ala Val Phe Asp Gly Ile Glu
                280                 285                 290 gtttgtgctt cgccttcatt atatgctctt tgctggtcaa ttccatttaa atgttaagat        3600
ctcttaggaa cgtttggatg accaagaaga agtgtttgct acaggataga acaaaatagt        3660
aggcatgtgt tagttaccaa acctgtaaac tgcttcttta ttcaattcgc caaaccatag        3720
accttaggaa gacttagatt tacaagagaa ttctctattc tcgaccaaaa accctagaca        3780
aaatccagaa taccctagg gctaattaca atgttcatgt acctatcaat atatatctcc        3840
tgctaagatt gtcttagctt tggtatagcc tagatatata tagataccgt aatttctaat        3900
gcatatttag aatgttttac ttaaactcag gctcttgctc ttctaaaact tgtacttcaa        3960
ttgttaaact aaaacctcag tatctgtctt agctaaagtt acttttactt gttttttcatt       4020 aagttgacct gtcaattgca cttgttcaca g ggc agt tat gta gcg gag aat           4072
                                  Gly Ser Tyr Val Ala Glu Asn
                                                        295
```

```
gta gag aga aat gat gaa ggg ccc ctg atg atg aat gcc ttt gag atg    4120
Val Glu Arg Asn Asp Glu Gly Pro Leu Met Met Asn Ala Phe Glu Met
300                 305                 310                 315 att acc tta tca caa ggc tta aat tta tct gca cta ttt gac agg cga    4168
Ile Thr Leu Ser Gln Gly Leu Asn Leu Ser Ala Leu Phe Asp Arg Arg
            320                 325                 330 cag gtagtacctg attttctatt actggtcata gagatctcca tttcgaataa         4221
Gln aagaatgtcg gtagcatcta ttcttcagac tgcccgtttt gactgcctta tgatgctgtg  4281
ttcttagttt gttataataa ctataagttc attagatgat tggttgcatg cattagtag   4341 atacaaatgg aatccaaaat gttcctgcat attgatggct gatcctttga tctcgcag    4399 gat ttt gtt aaa agg caa acc cgt ttt gtt tct cga agg gaa cct agt    4447
Asp Phe Val Lys Arg Gln Thr Arg Phe Val Ser Arg Arg Glu Pro Ser
        335                 340                 345 gag ata att gct aac att gag gct gta gcg aac tca atg ggt ttt aag    4495
Glu Ile Ile Ala Asn Ile Glu Ala Val Ala Asn Ser Met Gly Phe Lys
    350                 355                 360 tct cat aca cga aac ttc aag gtaacgaatt cctagcatat tacacttatc       4546
Ser His Thr Arg Asn Phe Lys
365                 370 acagagatta tgcattattt taaaactctc aactgttaaa cgcatgtgta gatagattga  4606
taagattgac aaggaaactt agtttatatc tctggcgttc aaaaacgaaa gtcctagtgt  4666
gaattatcat ttttaatgtt agcagagagt acaattgtta tgatttgtta cgtctatgtg  4726 ctcaacag aca agg ctc gag gga tta tct tcg atc aag gcc gga cag tta   4776
         Thr Arg Leu Glu Gly Leu Ser Ser Ile Lys Ala Gly Gln Leu
                 375                 380                 385 gct gtt gtg ata gag gtaattattg cttgttgtga ttgtaatata agtttgcttt    4831
Ala Val Val Ile Glu
            390 gcttcagttt aagggtatct agcaaattga aattaaccta catgcag att tac gag    4887
                                                    Ile Tyr Glu gtg gca cca tcg ctt ttc atg gta gac gta aga aag gct gct ggt gaa    4935
Val Ala Pro Ser Leu Phe Met Val Asp Val Arg Lys Ala Ala Gly Glu
395                 400                 405 act ctt gaa tat cac aag gtttataaat atatatccaa taacaatagt           4983
Thr Leu Glu Tyr His Lys
410                 415 tgcatcatta ctgtgttgcg gattagagtg atattttgtt ttgtggtatc gcag ttc    5040
                                                             Phe tac aag aag cta tgt tcg aaa ctg gaa aac ata ata tgg agg gca aca    5088
Tyr Lys Lys Leu Cys Ser Lys Leu Glu Asn Ile Ile Trp Arg Ala Thr
        420                 425                 430 gaa gga ata cca aag tca gag att ctc aga aca atc acg ttt            5130
Glu Gly Ile Pro Lys Ser Glu Ile Leu Arg Thr Ile Thr Phe
    435                 440                 445 tgatcccaac ttaa                                                    5144

<210> SEQ ID NO 2
<211> LENGTH: 446
<212> TYPE: PRT
<213> ORGANISM: Arabidopsis thaliana

<400> SEQUENCE: 2

Met Thr Lys Lys Met Arg Arg Val Gly Lys Tyr Glu Val Gly Arg Thr
1               5                   10                  15

Ile Gly Glu Gly Thr Phe Ala Lys Val Lys Phe Ala Arg Asn Thr Asp
```

-continued

```
                  20                  25                  30
Thr Gly Asp Asn Val Ala Ile Lys Ile Met Ala Lys Ser Thr Ile Leu
         35                  40                  45
Lys Asn Arg Met Val Asp Gln Ile Lys Arg Glu Ile Ser Ile Met Lys
     50                  55                  60
Ile Val Arg His Pro Asn Ile Val Arg Leu Tyr Glu Val Leu Ala Ser
 65                  70                  75                  80
Pro Ser Lys Ile Tyr Ile Val Leu Glu Phe Val Thr Gly Gly Glu Leu
                 85                  90                  95
Phe Asp Arg Ile Val His Lys Gly Arg Leu Glu Glu Ser Glu Ser Arg
            100                 105                 110
Lys Tyr Phe Gln Gln Leu Val Asp Ala Val His Cys His Cys Lys
        115                 120                 125
Gly Val Tyr His Arg Asp Leu Lys Pro Glu Asn Leu Leu Leu Asp Thr
        130                 135                 140
Asn Gly Asn Leu Lys Val Ser Asp Phe Gly Leu Ser Ala Leu Pro Gln
145                 150                 155                 160
Glu Gly Val Glu Leu Leu Arg Thr Thr Cys Gly Thr Pro Asn Tyr Val
                165                 170                 175
Ala Pro Glu Val Leu Ser Gly Gln Gly Tyr Asp Gly Ser Ala Ala Asp
            180                 185                 190
Ile Trp Ser Cys Gly Val Ile Leu Phe Val Ile Leu Ala Gly Tyr Leu
        195                 200                 205
Pro Phe Ser Glu Thr Asp Leu Pro Gly Leu Tyr Arg Lys Ile Asn Ala
    210                 215                 220
Ala Glu Phe Ser Cys Pro Pro Trp Phe Ser Ala Glu Val Lys Phe Leu
225                 230                 235                 240
Ile His Arg Ile Leu Asp Pro Asn Pro Lys Thr Arg Ile Gln Ile Gln
                245                 250                 255
Gly Ile Lys Lys Asp Pro Trp Phe Arg Leu Asn Tyr Val Pro Ile Arg
            260                 265                 270
Ala Arg Glu Glu Glu Val Asn Leu Asp Asp Ile Arg Ala Val Phe
        275                 280                 285
Asp Gly Ile Glu Gly Ser Tyr Val Ala Glu Asn Val Glu Arg Asn Asp
    290                 295                 300
Glu Gly Pro Leu Met Met Asn Ala Phe Glu Met Ile Thr Leu Ser Gln
305                 310                 315                 320
Gly Leu Asn Leu Ser Ala Leu Phe Asp Arg Arg Gln Asp Phe Val Lys
                325                 330                 335
Arg Gln Thr Arg Phe Val Ser Arg Arg Glu Pro Ser Glu Ile Ile Ala
            340                 345                 350
Asn Ile Glu Ala Val Ala Asn Ser Met Gly Phe Lys Ser His Thr Arg
        355                 360                 365
Asn Phe Lys Thr Arg Leu Glu Gly Leu Ser Ser Ile Lys Ala Gly Gln
    370                 375                 380
Leu Ala Val Val Ile Glu Ile Tyr Glu Val Ala Pro Ser Leu Phe Met
385                 390                 395                 400
Val Asp Val Arg Lys Ala Ala Gly Glu Thr Leu Glu Tyr His Lys Phe
                405                 410                 415
Tyr Lys Lys Leu Cys Ser Lys Leu Glu Asn Ile Ile Trp Arg Ala Thr
            420                 425                 430
Glu Gly Ile Pro Lys Ser Glu Ile Leu Arg Thr Ile Thr Phe
        435                 440                 445
```

<210> SEQ ID NO 3
<211> LENGTH: 633
<212> TYPE: PRT
<213> ORGANISM: Saccharomyces cerevisiae

<400> SEQUENCE: 3

Met Ser Ser Asn Asn Thr Asn Thr Ala Pro Ala Asn Ala Asn Ser
1               5                   10                  15

Ser His His His His His His His His His His Gly His
                20                  25                  30

Gly Gly Ser Asn Ser Thr Leu Asn Asn Pro Lys Ser Ser Leu Ala Asp
            35                  40                  45

Gly Ala His Ile Gly Asn Tyr Gln Ile Val Lys Thr Leu Gly Glu Gly
        50                  55                  60

Ser Phe Gly Lys Val Lys Leu Ala Tyr His Thr Thr Gly Gln Lys
65                  70                  75                  80

Val Ala Leu Lys Ile Ile Asn Lys Lys Val Leu Ala Lys Ser Asp Met
                85                  90                  95

Gln Gly Arg Ile Glu Arg Glu Ile Ser Tyr Leu Arg Leu Leu Arg His
            100                 105                 110

Pro His Ile Ile Lys Leu Tyr Asp Val Ile Lys Ser Lys Asp Glu Ile
        115                 120                 125

Ile Met Val Ile Glu Tyr Ala Gly Asn Glu Leu Phe Asp Tyr Ile Val
130                 135                 140

Gln Arg Asp Lys Met Ser Glu Gln Glu Ala Arg Arg Phe Phe Gln Gln
145                 150                 155                 160

Ile Ile Ser Ala Val Glu Tyr Cys His Arg His Lys Ile Val His Arg
                165                 170                 175

Asp Leu Lys Pro Glu Asn Leu Leu Asp Glu His Leu Asn Val Lys
            180                 185                 190

Ile Ala Asp Phe Gly Leu Ser Asn Ile Met Thr Asp Gly Asn Phe Leu
        195                 200                 205

Lys Thr Ser Cys Gly Ser Pro Asn Tyr Ala Ala Pro Glu Val Ile Ser
210                 215                 220

Gly Lys Leu Tyr Ala Gly Pro Glu Val Asp Val Trp Ser Cys Gly Val
225                 230                 235                 240

Ile Leu Tyr Val Met Leu Cys Arg Arg Leu Pro Phe Asp Asp Glu Ser
                245                 250                 255

Ile Pro Val Leu Phe Lys Asn Ile Ser Asn Gly Val Tyr Thr Leu Pro
            260                 265                 270

Lys Phe Leu Ser Pro Gly Ala Ala Gly Leu Ile Lys Arg Met Leu Ile
        275                 280                 285

Val Asn Pro Leu Asn Arg Ile Ser Ile His Glu Ile Met Gln Asp Asp
290                 295                 300

Trp Phe Lys Val Asp Leu Pro Glu Tyr Leu Leu Pro Pro Asp Leu Lys
305                 310                 315                 320

Pro His Pro Glu Glu Glu Asn Glu Asn Asn Asp Ser Lys Lys Asp Gly
                325                 330                 335

Ser Ser Pro Asp Asn Asp Glu Ile Asp Asp Asn Leu Val Asn Ile Leu
            340                 345                 350

Ser Ser Thr Met Gly Tyr Glu Lys Asp Glu Ile Tyr Glu Ser Leu Glu
        355                 360                 365

Ser Ser Glu Asp Thr Pro Ala Phe Asn Glu Ile Arg Asp Ala Tyr Met

```
              370                 375                 380
Leu Ile Lys Glu Asn Lys Ser Leu Ile Lys Asp Met Lys Ala Asn Lys
385                 390                 395                 400

Ser Val Ser Asp Glu Leu Asp Thr Phe Leu Ser Gln Ser Pro Pro Thr
                405                 410                 415

Phe Gln Gln Ser Lys Ser His Gln Lys Ser Gln Val Asp His Glu
                420                 425                 430

Thr Ala Lys Gln His Ala Arg Arg Met Ala Ser Ala Ile Thr Gln Gln
                435                 440                 445

Arg Thr Tyr His Gln Ser Pro Phe Met Asp Gln Tyr Lys Glu Glu Asp
                450                 455                 460

Ser Thr Val Ser Ile Leu Pro Thr Ser Leu Pro Gln Ile His Arg Ala
465                 470                 475                 480

Asn Met Leu Ala Gln Gly Ser Pro Ala Ala Ser Lys Ile Ser Pro Leu
                485                 490                 495

Val Thr Lys Lys Ser Lys Thr Arg Trp His Phe Gly Ile Arg Ser Arg
                500                 505                 510

Ser Tyr Pro Leu Asp Val Met Gly Glu Ile Tyr Ile Ala Leu Lys Asn
                515                 520                 525

Leu Gly Ala Glu Trp Ala Lys Pro Ser Glu Glu Asp Leu Trp Thr Ile
                530                 535                 540

Lys Leu Arg Trp Lys Tyr Asp Ile Gly Asn Lys Thr Asn Thr Asn Glu
545                 550                 555                 560

Lys Ile Pro Asp Leu Met Lys Met Val Ile Gln Leu Phe Gln Ile Glu
                565                 570                 575

Thr Asn Asn Tyr Leu Val Asp Phe Lys Phe Asp Gly Trp Glu Ser Ser
                580                 585                 590

Tyr Gly Asp Asp Thr Thr Val Ser Asn Ile Ser Glu Asp Glu Met Ser
                595                 600                 605

Thr Phe Ser Ala Tyr Pro Phe Leu His Leu Thr Thr Lys Leu Ile Met
                610                 615                 620

Glu Leu Ala Val Asn Ser Gln Ser Asn
625                 630

<210> SEQ ID NO 4
<211> LENGTH: 552
<212> TYPE: PRT
<213> ORGANISM: Homo sapiens

<400> SEQUENCE: 4

Met Ala Glu Lys Gln Lys His Asp Gly Arg Val Lys Ile Gly His Tyr
1               5                   10                  15

Val Leu Gly Asp Thr Leu Gly Val Gly Thr Phe Gly Lys Val Lys Ile
                20                  25                  30

Gly Glu His Gln Leu Thr Gly His Lys Val Ala Val Lys Ile Leu Asn
                35                  40                  45

Arg Gln Lys Ile Arg Ser Leu Asp Val Val Gly Lys Ile Lys Arg Glu
                50                  55                  60

Ile Gln Asn Leu Lys Leu Phe Arg His Pro His Ile Ile Lys Leu Tyr
65                  70                  75                  80

Gln Val Ile Ser Thr Pro Thr Asp Phe Phe Met Val Met Glu Tyr Val
                85                  90                  95

Ser Gly Gly Glu Leu Phe Asp Tyr Ile Cys Lys His Gly Arg Val Glu
                100                 105                 110
```

-continued

```
Glu Met Glu Ala Arg Arg Leu Phe Gln Gln Ile Leu Ser Ala Val Asp
        115                 120                 125

Tyr Cys His Arg His Met Val Val His Arg Asp Leu Lys Pro Glu Asn
    130                 135                 140

Val Leu Leu Asp Ala His Met Asn Ala Lys Ile Ala Asp Phe Gly Leu
145                 150                 155                 160

Ser Asn Met Met Ser Asp Gly Glu Phe Leu Arg Thr Ser Cys Gly Ser
                165                 170                 175

Pro Asn Tyr Ala Ala Pro Glu Val Ile Ser Gly Arg Leu Tyr Ala Gly
            180                 185                 190

Pro Glu Val Asp Ile Trp Ser Cys Gly Val Ile Leu Tyr Ala Leu Leu
        195                 200                 205

Cys Gly Thr Leu Pro Phe Asp Asp Glu His Val Pro Thr Leu Phe Lys
    210                 215                 220

Lys Ile Arg Gly Gly Val Phe Tyr Ile Pro Glu Tyr Leu Asn Arg Ser
225                 230                 235                 240

Val Ala Thr Leu Leu Met His Met Leu Gln Val Asp Pro Leu Lys Arg
                245                 250                 255

Ala Thr Ile Lys Asp Ile Arg Glu His Glu Trp Phe Lys Gln Gly Leu
            260                 265                 270

Pro Ser Tyr Leu Phe Pro Glu Asp Pro Ser Tyr Asp Ala Asn Val Ile
        275                 280                 285

Asp Asp Glu Ala Val Lys Glu Val Cys Glu Lys Phe Glu Cys Thr Glu
    290                 295                 300

Ser Glu Val Met Asn Ser Leu Tyr Ser Gly Asp Pro Gln Asp Gln Leu
305                 310                 315                 320

Ala Val Ala Tyr His Leu Ile Ile Asp Asn Arg Arg Ile Met Asn Gln
                325                 330                 335

Ala Ser Glu Phe Tyr Leu Ala Ser Ser Pro Ser Gly Ser Phe Met
            340                 345                 350

Asp Asp Ser Ala Met His Ile Pro Pro Gly Leu Lys Pro His Pro Glu
        355                 360                 365

Arg Met Pro Pro Leu Ile Ala Asp Ser Pro Lys Ala Arg Cys Pro Leu
    370                 375                 380

Asp Ala Leu Asn Thr Thr Lys Pro Lys Ser Leu Ala Val Lys Lys Ala
385                 390                 395                 400

Lys Trp His Leu Gly Ile Arg Ser Gln Ser Lys Pro Tyr Asp Ile Met
                405                 410                 415

Ala Glu Val Tyr Arg Ala Met Lys Gln Leu Asp Phe Glu Trp Lys Val
            420                 425                 430

Val Asn Ala Tyr His Leu Arg Val Arg Arg Lys Asn Pro Val Thr Gly
        435                 440                 445

Asn Tyr Val Lys Met Ser Leu Gln Leu Tyr Leu Val Asp Asn Arg Ser
    450                 455                 460

Tyr Leu Leu Asp Phe Lys Ser Ile Asp Asp Glu Val Val Glu Gln Arg
465                 470                 475                 480

Ser Gly Ser Ser Thr Pro Gln Arg Ser Cys Ser Ala Ala Gly Leu His
                485                 490                 495

Arg Pro Arg Ser Ser Phe Asp Ser Thr Thr Ala Glu Ser His Ser Leu
            500                 505                 510

Ser Gly Ser Leu Thr Gly Ser Leu Thr Gly Ser Thr Leu Ser Ser Val
        515                 520                 525

Ser Pro Arg Leu Gly Ser His Thr Met Asp Phe Phe Glu Met Cys Ala
```

-continued

Ser Leu Ile Thr Thr Leu Ala Arg
545                 550

<210> SEQ ID NO 5
<211> LENGTH: 496
<212> TYPE: PRT
<213> ORGANISM: Schizosaccharomyces pombe

<400> SEQUENCE: 5

Met Ala Gln Lys Leu Asp Asn Phe Pro Tyr His Ile Gly Arg Glu Ile
1               5                   10                  15

Gly Thr Gly Ala Phe Ala Ser Val Arg Leu Cys Tyr Asp Asp Asn Ala
            20                  25                  30

Lys Ile Tyr Ala Val Lys Phe Val Asn Lys Lys His Ala Thr Ser Cys
        35                  40                  45

Met Asn Ala Gly Val Trp Ala Arg Arg Met Ala Ser Glu Ile Gln Leu
    50                  55                  60

His Lys Leu Cys Asn Gly His Lys Asn Ile Ile His Phe Tyr Asn Thr
65                  70                  75                  80

Ala Glu Asn Pro Gln Trp Arg Trp Val Val Leu Glu Phe Ala Gln Gly
                85                  90                  95

Gly Asp Leu Phe Asp Lys Ile Glu Pro Asp Val Gly Ile Asp Glu Asp
            100                 105                 110

Val Ala Gln Phe Tyr Phe Ala Gln Leu Met Glu Gly Ile Ser Phe Met
        115                 120                 125

His Ser Lys Gly Val Ala His Arg Asp Leu Lys Pro Glu Asn Ile Leu
    130                 135                 140

Leu Asp Tyr Asn Gly Asn Leu Lys Ile Ser Asp Phe Gly Phe Ala Ser
145                 150                 155                 160

Leu Phe Ser Tyr Lys Gly Lys Ser Arg Leu Leu Asn Ser Pro Val Gly
                165                 170                 175

Ser Pro Pro Tyr Ala Ala Pro Glu Ile Thr Gln Gln Tyr Asp Gly Ser
            180                 185                 190

Lys Val Asp Val Trp Ser Cys Gly Ile Ile Leu Phe Ala Leu Leu Leu
        195                 200                 205

Gly Asn Thr Pro Trp Asp Glu Ala Ile Ser Asn Thr Gly Asp Tyr Leu
    210                 215                 220

Leu Tyr Lys Lys Gln Cys Glu Arg Pro Ser Tyr His Pro Trp Asn Leu
225                 230                 235                 240

Leu Ser Pro Gly Ala Tyr Ser Ile Ile Thr Gly Met Leu Arg Ser Asp
                245                 250                 255

Pro Phe Lys Arg Tyr Ser Val Lys His Val Val Gln His Pro Trp Leu
            260                 265                 270

Thr Ser Ser Thr Pro Phe Arg Thr Lys Asn Gly Asn Cys Ala Asp Pro
        275                 280                 285

Val Ala Leu Ala Ser Arg Leu Met Leu Lys Leu Arg Ile Asp Leu Asp
    290                 295                 300

Lys Pro Arg Leu Ala Ser Ser Arg Ala Ser Gln Asn Asp Ser Gly Phe
305                 310                 315                 320

Ser Met Thr Gln Pro Ala Phe Lys Lys Asn Asp Gln Lys Glu Leu Asp
                325                 330                 335

Arg Val Glu Val Tyr Gly Ala Leu Ser Gln Pro Val Gln Leu Asn Lys
            340                 345                 350

-continued

Asn Ile Asp Val Thr Glu Ile Leu Glu Lys Asp Pro Ser Leu Ser Gln
        355                 360                 365

Phe Cys Glu Asn Glu Gly Phe Ile Lys Arg Leu Ala Lys Lys Ala Lys
    370                 375                 380

Asn Phe Tyr Glu Ile Cys Pro Pro Glu Arg Leu Thr Arg Phe Tyr Ser
385                 390                 395                 400

Arg Ala Ser Arg Glu Thr Ile Ile Asp His Leu Tyr Asp Ser Leu Arg
                405                 410                 415

Leu Leu Ala Ile Ser Val Thr Met Lys Tyr Val Arg Asn Gln Thr Ile
            420                 425                 430

Leu Tyr Val Asn Leu His Asp Lys Arg Lys Cys Leu Leu Gln Gly Val
        435                 440                 445

Ile Glu Leu Thr Asn Leu Gly His Asn Leu Glu Leu Ile Asn Phe Ile
    450                 455                 460

Lys Arg Asn Gly Asp Pro Leu Glu Trp Arg Lys Phe Phe Lys Asn Val
465                 470                 475                 480

Val Ser Ser Ile Gly Lys Pro Ile Val Leu Thr Asp Val Ser Gln Asn
                485                 490                 495

<210> SEQ ID NO 6
<211> LENGTH: 476
<212> TYPE: PRT
<213> ORGANISM: Homo sapiens

<400> SEQUENCE: 6

Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
                20                  25                  30

Glu Ala Val Ala Val Lys Ile Val Asp Met Lys Arg Ala Val Asp Cys
            35                  40                  45

Pro Glu Asn Ile Lys Lys Glu Ile Cys Ile Asn Lys Met Leu Asn His
        50                  55                  60

Glu Asn Val Val Lys Phe Tyr Gly His Arg Arg Glu Gly Asn Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
                100                 105                 110

Gln Leu Met Ala Gly Val Val Tyr Leu His Gly Ile Gly Ile Thr His
            115                 120                 125

Arg Asp Ile Lys Pro Glu Asn Leu Leu Leu Asp Glu Arg Asp Asn Leu
130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

```
Leu Leu His Lys Ile Leu Val Glu Asn Pro Ser Ala Arg Ile Thr Ile
                245                 250                 255
Pro Asp Ile Lys Lys Asp Arg Trp Tyr Asn Lys Pro Leu Lys Lys Gly
            260                 265                 270
Ala Lys Arg Pro Arg Val Thr Ser Gly Gly Val Ser Glu Ser Pro Ser
        275                 280                 285
Gly Phe Ser Lys His Ile Gln Ser Asn Leu Asp Phe Ser Pro Val Asn
    290                 295                 300
Ser Ala Ser Ser Glu Glu Asn Val Lys Tyr Ser Ser Ser Gln Pro Glu
305                 310                 315                 320
Pro Arg Thr Gly Leu Ser Leu Trp Asp Thr Ser Pro Ser Tyr Ile Asp
                325                 330                 335
Lys Leu Val Gln Gly Ile Ser Phe Ser Gln Pro Thr Cys Pro Asp His
            340                 345                 350
Met Leu Leu Asn Ser Gln Leu Leu Gly Thr Pro Gly Ser Ser Gln Asn
        355                 360                 365
Pro Trp Gln Arg Leu Val Lys Arg Met Thr Arg Phe Phe Thr Lys Leu
    370                 375                 380
Asp Ala Asp Lys Ser Tyr Gln Cys Leu Lys Glu Thr Cys Glu Lys Leu
385                 390                 395                 400
Gly Tyr Gln Trp Lys Lys Ser Cys Met Asn Gln Val Thr Ile Ser Thr
                405                 410                 415
Thr Asp Arg Arg Asn Asn Lys Leu Ile Phe Lys Val Asn Leu Leu Glu
            420                 425                 430
Met Asp Asp Lys Ile Leu Val Asp Phe Arg Leu Ser Lys Gly Asp Gly
        435                 440                 445
Leu Glu Phe Lys Arg His Phe Leu Lys Ile Lys Gly Lys Leu Ile Asp
    450                 455                 460
Ile Val Ser Ser Gln Lys Val Trp Leu Pro Ala Thr
465                 470                 475
```

<210> SEQ ID NO 7
<211> LENGTH: 35
<212> TYPE: DNA
<213> ORGANISM: Artificial Sequence
<220> FEATURE:
<223> OTHER INFORMATION: Synthetic DNA

<400> SEQUENCE: 7
gcggatccat gacaaagaaa atgagaagag tgggc       35

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
attgtactct tagccataat gttgatggct       30

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9

```
gcgaattctt aagttgggat caaaacgtga ttgttctg                        38

<210> SEQ ID NO 10
<211> LENGTH: 30
<212> TYPE: DNA
<213> ORGANISM: Artificial Sequence
<220> FEATURE:
<223> OTHER INFORMATION: Synthetic DNA

<400> SEQUENCE: 10
gtgataatgt agccatcaac attatggcta                                 30

<210> SEQ ID NO 11
<211> LENGTH: 35
<212> TYPE: DNA
<213> ORGANISM: Artificial Sequence
<220> FEATURE:
<223> OTHER INFORMATION: Synthetic DNA

<400> SEQUENCE: 11
gcggatccat gacaaagaaa atgagaagag tgggc                           35

<210> SEQ ID NO 12
<211> LENGTH: 30
<212> TYPE: DNA
<213> ORGANISM: Artificial Sequence
<220> FEATURE:
<223> OTHER INFORMATION: Synthetic DNA

<400> SEQUENCE: 12
atataacgaa aagaataacc tcgcaagacc                                 30

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
gctgatattt ggtcttgcga ggttattctt                                 30

<210> SEQ ID NO 14
<211> LENGTH: 38
<212> TYPE: DNA
<213> ORGANISM: Artificial Sequence
<220> FEATURE:
<223> OTHER INFORMATION: Synthetic DNA

<400> SEQUENCE: 14
gcgaattctt aagttgggat caaaacgtga ttgttctg                        38

<210> SEQ ID NO 15
<211> LENGTH: 35
<212> TYPE: DNA
<213> ORGANISM: Artificial Sequence
<220> FEATURE:
<223> OTHER INFORMATION: Synthetic DNA

<400> SEQUENCE: 15
gcggatccat gacaaagaaa atgagaagag tgggc                           35

<210> SEQ ID NO 16
<211> LENGTH: 38
<212> TYPE: DNA
```

```
<213> ORGANISM: Artificial Sequence
<220> FEATURE:
<223> OTHER INFORMATION: Synthetic DNA

<400> SEQUENCE: 16
gcgaattctt aagttgggat caaaacgtga ttgttctg                              38
```

PROTEINS AND DNA RELATED TO SALT TOLERANCE IN PLANTS

CROSS-REFERENCE TO RELATED APPLICATIONS

This application claims benefit to U.S. provisional application No. 60/194,649, filed on Apr. 04, 2000, and incorporated herein by reference in its entirety.

STATEMENT OF FEDERALLY FUNDED RESEARCH

This invention was supported by the National Institutes Health by Contract No. R01GM59138 and the U.S. Department of Agriculture by Contract No. 9801270. The government may have certain rights to this invention.

BACKGROUND OF THE INVENTION

1. Field of the Invention

The present invention relates to proteins and nucleic acids related to salt tolerance in plants.

2. Description of the Background

In *Arabidopsis thaliana*, the Salt Overly Sensitive 2 (SOS2) gene is required for intracellular $Na^+$ and $K^+$ homeostasis. Mutations in SOS2 cause $Na^+$ and $K^+$ imbalance and render plants more sensitive toward growth inhibition by high $Na^+$ and low $K^+$ environments. We isolated the SOS2 gene through positional cloning. SOS2 is predicted to encode a serine/threonine type protein kinase with an N-terminal catalytic domain similar to that of the yeast SNF1 kinase. Sequence analyses of sos2 mutant alleles reveal that both the N-terminal catalytic domain and the C-terminal regulatory domain of SOS2 are functionally essential. The steady-state level of SOS2 transcript is up-regulated by salt stress in the root. Autophosphorylation assays show that SOS2 is an active protein kinase. In the recessive sos2-5 allele, a conserved glycine residue in the kinase catalytic domain is changed to glutamate. This mutation abolishes SOS2 autophosphorylation, indicating that SOS2 protein kinase activity is required for salt tolerance.

Control of intracellular ion homeostasis is essential for all cellular organisms. Most cells maintain relatively high $K^+$ and low $Na^+$ concentrations in the cytosol. In plants, this is achieved through coordinated regulation of transporters for $H^+$, $K^+$, and $Na^+$. At the plasma membrane, a family of P-type $H^+$-ATPases serves as the primary pump that generates a protonmotive force driving the active transport of other solutes, including $K^+$ and $Na^+$ (1). Several plant $K^+$ channels and transporters have been molecularly characterized. The inward rectifying $K^+$ channel AKT1 is essential for root $K^+$ uptake in *Arabidopsis thaliana* (2, 3). Expression characteristics indicate that the KAT1 channel is involved in $K^+$ influx in Arabidopsis guard cells (4, 5). Recently, an outward rectifying $K^+$ channel has been shown to be essential for unloading $K^+$ into the Arabidopsis root xylem (6). The wheat HKT1 gene product functions as a high-affinity $K^+$ transporter (7). In addition, a family of KUP genes exists in Arabidopsis. At least one of them, KUP1, encodes a protein that can function as a dual-affinity $K^+$ transporter (8, 9). $Na^+$ enters plant cells passively, presumably through $K^+$ transport systems (10), Unlike animals or fungi. plants do not seem to possess $Na^+/K^+$-ATPases or $Na^+$-ATPases. $Na^+$ efflux is achieved through the activities of $Na^+/H^+$ antiporters on the plasma membrane. Much of the $Na^+$ that enters the cell is compartmentalized into the vacuole through the action of vacuolar $Na^+/H^+$ antiporters (11, 12). The driving force for the vacuolar transporters is the protonmotive force created by vacuolar V-type $H^+$-ATPases and the $H^+$-pyrophosphatase (1, 13). Although there has been great progress in the characterization of $K^+$ and $Na^+$ transporters in plants, little is currently known about their regulation.

In the trophic chain, plant roots play pivotal roles by taking up mineral nutrients from soil solutions. Plant roots experience constant fluctuations in soil environments. A frequent variant in the soil solution is $Na^+$ concentration (14). $Na^+$ is not an essential ion for most plants. In fact, the growth of the majority of plants, glycophytes, is inhibited by the presence of high concentrations of soil $Na^+$. External $Na^+$ causes $K^+$ deficiency by inhibiting $K^+$ uptake into plant cells (15). $Na^+$ accumulation within the cell is toxic to many cytosolic enzymes. In contrast, many cellular enzymes are activated by $K^+$, which is the most abundant cation in the cytoplasm. Certain cytoplasmic enzymes arc especially prone to $Na^+$ inhibition when $K^+$ concentration is reduced (16). Therefore, maintaining intracellular $K^+$ and homeostasis to preserve a high $K^+/Na^+$ ratio is important for all cells and especially critical for plant cells.

A family of *Arabidopsis sos* (salt overly sensitive) mutants defective in the regulation of intracellular $Na^+$ and $K^+$ homeostasis was recently characterized (15, 17, 18). The sos mutants are specifically hypersensitive to inhibition by high concentrations of external $Na^+$ or $Li^-$ (17, 18). In response to high $Na^+$ challenge, the sos2 and sos3 mutants accumulate more $Na^+$ and retain less $K^+$ than wild-type plants (18). The mutants are also unable to grow when the external $K^+$ concentration is very low (17, 18). These phenotypes suggest that the mutant plants are defective in the regulation of $K^+$ and $Na^+$ transport (18). The SOS3 gene was recently cloned and shown to encode an EF hand-type calcium-binding protein that shares significant sequence similarities with animal neuronal calcium sensors and the yeast calcineurin B subunit (19). In yeast, calcineurin is a central component in the signaling pathway that regulates $Na^+$ and $K^-$ homeostasis (20, 21). Loss-of-function mutations in calcineurin B cause increased sensitivity of yeast cells to $Na^+$ or $Li^+$ stress.

Because of limited water supplies and the widespread use of irrigation, the soils of many cultivated areas have become increasingly salinized. In particular, modern agricultural practices such as irrigation impart increasing salt concentrations when the available irrigation water evaporates and leaves previously dissolved salts behind. As a result, the development of salt tolerant cultivars of agronomically important crops has become important in many parts of the world. For example, in salty soil found in areas such as Southern California, Arizona, New Mexico and Texas.

Dissolved salts in the soil increase the osmotic pressure of the solution in the soil and tend to decrease the rate at which water from the soil will enter the roots. If the solution in the soil becomes too saturated with dissolved salts, the water may actually be withdrawn from the plant roots. Thus the plants slowly starve though the supply of water and dissolved nutrients may be more than ample. Also, elements such as sodium are known to be toxic to plants when they are taken up by the plants.

Salt tolerant plants can facilitate use of marginal areas for crop production, or allow a wider range of sources of irrigation water. Traditional plant breeding methods have, thus far, not yielded substantial improvements in salt tolerance and growth of crop plants. In addition, such methods require long term selection and testing before new cultivars can be identified.

Accordingly, there is a need to increase salt tolerance in plants, particularly those plants which are advantageously useful as agricultural crops.

SUMMARY OF THE INVENTION

We report here the positional cloning of the SOS2 locus. SOS2 is predicted to encode a serine/threonine type protein kinase with an N-terminal catalytic domain highly similar to those of yeast SNF1 and mammalian AMPK kinases. Sequence analyses of several sos2 mutant alleles point to a functional requirement of both the N-terminal catalytic domain and the C-terminal regulatory domain of SOS2. SOS2 is expressed in both the root and shoot. In the root, SOS2 mRNA is up-regulated by salt stress. Autophosphorylation assays demonstrate that SOS2 is an active protein kinase. Furthermore, a mutation that abolishes SOS2 autophosphorylation renders plants hypersensitive to salt stress, indicating that SOS2 protein kinase activity is necessary for salt tolerance. This demonstrates that a protein kinase is essential for intracellular $Na^+$ and $K^+$ homeostasis and plant salt tolerance.

Thus, the present invention provides an isolated polynucleotide which encodes a protein comprising the amino acid sequence in SEQ ID NO:2.

In a preferred embodiment the polypeptide has serine/threonine kinase activity.

In another preferred embodiment the polynucleotide comprises SEQ ID NO:1, polynucleotides which are complimentary to SEQ ID NO:1, polynucleotides which are at least 70%, 80% and 90% identical to SEQ ID NO:1; or those sequence which hybridize under stringent conditions to SEQ ID NO:1, the stringent conditions comprise washing in 5 X SSC at a temperature from 50 to 68° C.

In another preferred embodiment the polynucleotides of the present invention are in a vector and/or a host cell. Preferably, the polynucleotides are in a plant cell or transgenic plant. Preferably, the plant is Arabidopsis thaliania or selected from the group consisting of wheat, corn, peanut cotton, oat, and soybean plant. In a preferred embodiment, the polynucleotides are operably linked to a promoter, preferably an inducible promoter.

In another preferred embodiment the present invention provides, a process for screening for polynucleotides which encode a protein having serine/threonine kinase activity comprising hybridizing the polynucleotide of the invention to the polynucleotide to be screened; expressing the polynucleotide to produce a protein; and detecting the presence or absence of serine/threonine kinase activity in said protein.

In another preferred embodiment, the present invention provides a method for detecting a nucleic acid with at least 70% homology to nucleotide SEQ ID NO:1, sequences which are complimentary to SEQ ID NO:1 and/or which encode a protein having the amino acid sequence in SEQ ID NO:2 comprising contacting a nucleic acid sample with a probe or primer comprising at least 15 consecutive nucleotides of the nucleotide sequence of claim 1, or at least 15 consecutive nucleotides of the complement thereof.

In another preferred embodiment, the present invention provides a method for producing a nucleic acid with at least 70% homology to the polynucleotides of the present invention comprising contacting a nucleic acid sample with a primer comprising at least 15 consecutive nucleotides of the nucleotide sequence of claim 3, or at least 15 consecutive nucleotides of the complement thereof.

In another preferred embodiment, the present invention provides a method for making SOS2 protein, comprising culturing the host cell carrying the polynucleotides of the invention for a time and under conditions suitable for expression of SOS2, and collecting the SOS2 protein.

In another preferred embodiment, the present invention provides a method of making a transgenic plant comprising introducing the polynucleotides of the invention into the plant.

In another preferred embodiment, the present invention provides method of increasing the salt tolerance of a plant in need thereof, comprising introducing the polynucleotides of the invention into said plant.

In another preferred embodiment, the present invention provides an isolated polypeptide comprising the amino acid sequence in SEQ ID NO:2 or those proteins that are at least 70%, preferably 80%, preferably 90% and preferably 95% identity to SEQ ID NO:2. Preferably, the polypeptides have serine/therenine kinase activity.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 2: SOS2 encodes a putative serine/threonine protein kinase. (A) Diagrammatic representation of SOS2 structure. (B) SOS2 cDNA sequence and the conceptual translation product (SEQ ID NO:2) of its longest ORF (GenBank accession number AF 237670). Underlined is a stop codon (TAA) at -6 to -4 that precedes the ATG in-frame. Numbers I–XI indicate kinase subdomains as defined by Hanks et al. (25), with invariant and nearly invariant amino acid residues highlighted in black and gray, respectively.

FIG. 3: Amino acid alignments. (A) Alignment of putative kinase catalytic domain of SOS2 with Saccharomyces cerevisiae SNF1 SEQ ID NO:3, (23) and human AMPK kinases, SEQ ID NO:4 (24). Amino acid residues identical in at least two proteins are highlighted in black and conservative substitutions in gray. Mutations that abolish SOS2 autophosphorylation (see FIG. 4) are indicated; first * is K40N,m and second is * G197E, which corresponds to the sos2-5 allele. (B) Alignment of the C-terminal portion of SOS2 with the regulatory domains of Schizosaccharomyces pombe (yCHK1, SEQ ID NO:5) and human CHK1 (hCHK1, SEQ ID NO:6) kinases (27).

DETAILED DESCRIPTION OF THE INVENTION

Figure 1A:
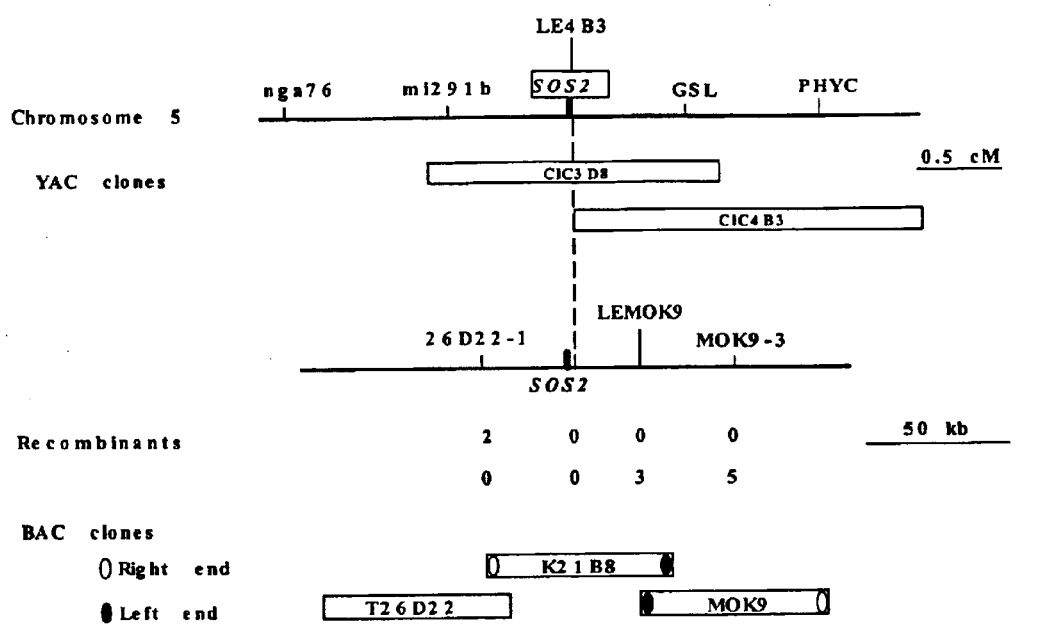
FIG. 1: Positional cloning of the SOS2 gene. (A) Physical mapping of SOS2. Genetic mapping delimited SOS2 to a region in the BAC clone K21B8. The SOS2 gene was identified by sequencing candidate genes in this region from sos2 mutant and wild-type plants. (B) Structure of SOS2 and position of sos2 mutations. Positions are relative to the initiation codon. Filled boxes indicate the ORF, and the lines between boxes indicate introns.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants. Preferred plants include rice, corn, wheat, cotton, peanut, and soybean.

Thus, in one embodiment of the present invention, the salt tolerance of a plant can be enhanced or increased by increasing the amount of protein available in the plant, preferably by the enhancement of the SOS2 gene in the plant.

Thus, one embodiment of the present invention are plant cells carrying the polynucleotides of the present invention, and preferably transgenic plants carrying the isolated polynucleotides of the present invention.

As used herein, the term "enhancement" means increasing the intracellular activity of one or more enzymes in a plant cell and/or plant which are encoded by the corresponding DNA. Enhancement can be achieved with the aid of various manipulations of the bacterial cell. In order to achieve enhancement, particularly over-expression, the number of copies of the corresponding gene can be increased, a strong promoter can be used, or the promoter and regulation region or the ribosome binding site which is situated upstream of the structural gene can be mutated. Expression cassettes which are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, enzyme activity as a whole is increased by preventing the degradation of the enzyme. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

A gene can also be used which encodes a corresponding or variant enzyme with a high activity. Preferably the corresponding enzyme has a greater activity than the native form of the enzyme, more preferably at least in the range of 5, 10, 25% or 50% more activity, most preferably more than twice the activity of the native enzyme.

In the context of the present Application, a polynucleotide sequence is "homologous" with the sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% of which, corresponds to the amino acid sequence which is encoded by the SOS2 gene (SEQ ID No.1), wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to polynucleotides which contain the complete gene with the polynucleotide sequence corresponding to SEQ ID No. 1 or fragments thereof, and which can be obtained by screening by means of the hybridization of a corresponding gene bank with a probe which contains the sequence of said polynucleotide corresponding to SEQ ID No. 1 or a fragment thereof, and isolation of said DNA sequence.

Polynucleotide sequences according to the invention are suitable as hybridization probes for RNA, cDNA and DNA, in order to isolate those cDNAs or genes which exhibit a high degree of similarity to the sequence of the SOS2 gene.

Polynucleotide sequences according to the invention are also suitable as primers for polymerase chain reaction (PCR) for the production of DNA which encodes an enzyme having activity of a serine/threonine kinase.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The polypeptides according to invention include polypeptides corresponding to SEQ ID No. 2, particularly those with the biological activity of a serine/threonine kinase, and also includes those, at least 70% of which, preferably at least 80% of which, are homologous with the polypeptide corresponding to SEQ ID No. 2, and most preferably those which exhibit a homology of least 90% to 95% with the polypeptide corresponding to SEQ ID No. 2 and which have the cited activity.

The invention also relates to coding DNA sequences which result from SEQ ID No. 1 by degeneration of the genetic code. In the same manner, the invention further relates to DNA sequences which hybridize with SEQ ID No. 1 or with parts of SEQ ID No. 1. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilise said function.

In the same manner, the present invention also relates to DNA sequences which hybridize with SEQ ID No. 1 or with parts of SEQ ID No. 1. Finally, the present invention relates to DNA sequences which are produced by polymerase chain reaction (PCR) using oligonucleotide primers which result from SEQ ID No. 1. Oligonucleotides of this type typically have a length of at least 15 nucleotides.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1X to 2X SSC (20X SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5X to 1X SSC at 55 to 60° C. Exemplary high stringency conditions include hybridization in 50% formamide, 1 M NaCl, 1% SDS at 37° C., and a wash in 0.1X SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl, Anal. Biochem., 138:267–284 (1984): $Tm=81.5° C.+16.6(\log M)+0.41(\%GC)-0.61 (\% form)-500/L$; where M is the molarity of monovalent cations, %GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000). Thus, with the foregoing information, the skilled artisan can identify and isolated polynucleotides which are substantially similar to the present polynucleotides. In so isolating such a polynucleotide, the polynucleotide can be used as the present polynucleotide in, for example, increasing the salt tolerance of a plant.

One embodiment of the present invention is methods of screening for polynucleotides which have substantial homology to the polynucleotides of the present invention, preferably those polynucleotides encoding a protein having serine/threonine kinase activity.

The polynucleotide sequences of the present invention can be carried on one or more suitable plasmid vectors, as known in the art for plants or the like.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

Materials and Methods

Genetic and Physical Mapping. Genetic mapping with restriction fragment length polymorphism and PCR-based markers was as described (19). Construction of yeast artificial chromosome (YAC) and bacterial artificial chromosome (BAC) clone contigs (1) was partly based on information available at publicly available databases. This information is incorporated herein by reference.

Nucleic Acid Analysis. For sequence determination, DNA was amplified from wild-type plants and sos2 mutants by PCR. Nine sos2 mutants alleles are known (18). All of the alleles were analyzed except sos24 and sos2-9 because viable seeds were not available. To avoid errors resulting from PCR, the products of five independent PCRs were pooled and sequenced. Reverse transcription-PCR was carried out on mRNA isolated from 2-week-old Arabidopsis seedlings. Salt stress treatment, RNA extraction, and Northern blot analysis were carried out as described by Ishitani et al. (22).

Protein Expression. To produce bacterially expressed recombinant proteins, the coding region of SOS2, SOS2 (K40N), and SOS2(G197E) cDNAs were amplified by PCR with primers harboring restriction sites, cloned in frame into BamHI-EcoRI of pGEX-2TK (Amersham Pharmacia), and transformed into *Escherichia coli* BL21 DE3 cells (Amersham Pharmacia). Mutations K40N and G197E in the SOS2 protein were created by site-directed mutagenesis. For glutathione S-transferase (GST)-SOS2(K40N), primer pairs 5'-GCGGATCCATGACAAAGAAAATGAGAAGAGTGGGC and (SEQ ID NO:7) 5'-ATTGTACTCTTAGCCATAAT-GTTGATGGCT (SEQ ID NO:8) were used for the first PCR, and 5'-GCGAATTCTTAAGTTGGGATCAAAA-CGTGATTGTTCTG (SEQ ID N):9) and 5'-GTGATAATGTAGCCATCAACATTATGGCTA (SEQ ID NO:10) were used for the second PCR. For the mutant protein GST-SOS2 (G197E), primer pairs 5'-GCGGATCCATGACAAAGAAAATGAGAAGAGT-GGC (SEQ ID NO:11) and 5'-ATATAACGAAAA-GAATAACCTCGCAAGACC (SEQ ID NO:12) were used for the first reaction and 5'-GCTGATATTTGGTCTTGC-GAGGTTATTCTT (SEQ ID NO:13) and 5'-GCGAAT-TCTTAAGTTGGGATCAAAACGTGATTGTTCTG (SEQ ID NO:14) were used for the second reaction. The final amplification was done with 5'-GCGGATCCATGA-CAAAGAAAATGAGAAGAGTGGGC (SEQ ID NO:15) and 5'-GCGAATTCTTAAGTTGGGATCAAAACGTGA-TTGTTCTG (SEQ ID NO:16) on both templates. The final constructs were confirmed by sequencing *E. coli* cultures were induced with 0.5 mM isopropyl β-D-thiogalactoside, and recombinant proteins were affinity-purified from bacterial lysates with glutathione-Sepharose beads (Amersham Pharmacia).

Kinase Assay. GST-fusion proteins were incubated in kinase buffer [20 mM Tris-HCl (pH 8.0)/5 mM $MgCl_2$/1 mM $CaCl_2$/1 mM DTT]. The kinase reaction was started by adding [$\gamma$-$^{32}$P] ATP and was transferred to 30° C. for 30 min. The reaction was stopped by adding 4X SDS-sample buffer and analyzed by SDS/PAGE and autoradiography.

Results

Figure 1B:
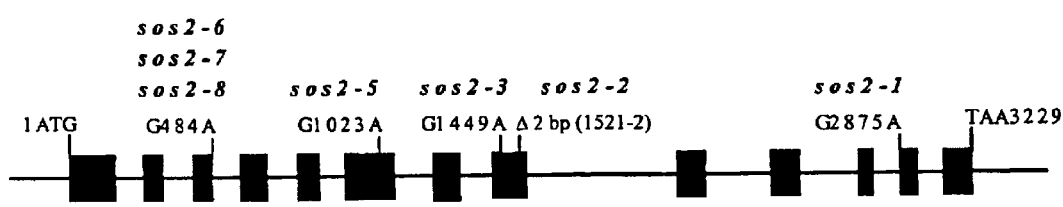

Positional Cloning of SOS2. The SOS2 gene was mapped by crossing the sos2-2/sos2-2 mutant, which is in the Columbia ecotype, to the SOS2/SOS2 Landsberg ecotype. On the basis of analysis of 1230 recombinant chromosomes, the SOS2 locus was previously mapped to chromosome V, between molecular markers nga76 and PHYC (18). Further genetic mapping using the recombination crossover points narrowed SOS2 to a region between the restriction fragment length polymorphism markers mi291b and GSL (FIG. 1A). A YAC contig covering this region was assembled. The left end of YAC CIC4B3 (LE4B3) was found to be tightly linked to SOS2 because no recombination occurred (FIG. 1A). A contig of BAC clones centered around LE4B3 was assembled. Simple sequence length polymorphism markers 26D22-1 and MOK9-3 and single nucleotide polymorphism marker LEMOK9 were developed based on sequence information of the respective BAC clones. Genetic mapping using these markers delimited the SOS2 locus to a 60-kb region of K21B8. Sequence analysis revealed that a candidate gene within this region carries a 2-bp deletion in the sos2-2 allele, which was generated by fast neutron irradiation (FIG. 1B). Further sequence analyses revealed that other sos2 alleles all carry mutations in this gene (FIG. 1B). Each mutation causes a change in amino acid sequence in the predicted ORF. We therefore conclude that this candidate is the SOS2 gene.

SOS2 Encodes a Protein Kinase. The transcribed sequence of the SOS2 gene was determined by sequencing cDNAs obtained by reverse transcription-PCR. Comparison with the genomic sequence showed that the SOS2 gene contains 13 exons and 12 introns (FIG. 1B). SOS2 is predicted to encode a protein of 446 amino acids with an estimated molecular mass of 51 kDa (FIG. 2). Database searches revealed that the deduced amino acid sequence of SOS2 has similarity with various serine/threonine protein kinases. The putative kinase catalytic domain of SOS2 resides in the N-terminal portion of the protein (FIG. 2A) and contains the 11 subdomains common to protein kinases (25). The putative catalytic domain sequence is most similar to the yeast SNF1 and mammalian AMPK kinases (23, 24) (FIG. 3A). The sos2-5, sos2-6, sos2-7, and sos2-8 mutations are predicted to disrupt the kinase catalytic domain. In the sos2-5 allele, Gly-197, which corresponds to one of the invariant amino acid residues of subdomain IX of protein kinases (25, 26), is changed to a negatively charged glutamic acid residue. sos2-6, sos2-7, and sos2-8 are identical mutations that disrupt the donor site of an intron splice junction (FIG. 1B), resulting in mal-splicing, premature termination, and a truncated polypeptide of 130 amino acid residues.

The C-terminal putative regulatory domain of SOS2 is relatively unique. Part of this domain of SOS2 shows low sequence homology with the regulatory domains of DNA replication checkpoint kinase CHK1 from yeast and humans (27-29) (FIG. 3B). Analysis of the other sos2 mutant alleles revealed that the mutations disrupt only the putative regulatory domain, leaving the catalytic domain intact. This suggests an essential function of the putative regulatory domain in plant $Na^+$ tolerance. In the sos2-1 mutant allele, a single base pair substitution at the acceptor site of an intron splicing junction results in the addition of 29 amino acid residues between Glu-390 and Ile-391, presumably disrupting the function of the putative regulatory domain. The sos2-2 mutation that was created by fast neutron bombardment (18) has a 2-bp deletion that causes frameshift and premature termination, resulting in a truncated polypeptide of 287 amino acids. In the sos2-3 mutant allele, a single nucleotide substitution creates a stop codon that truncates the protein at Pro-262.

Figure 4:
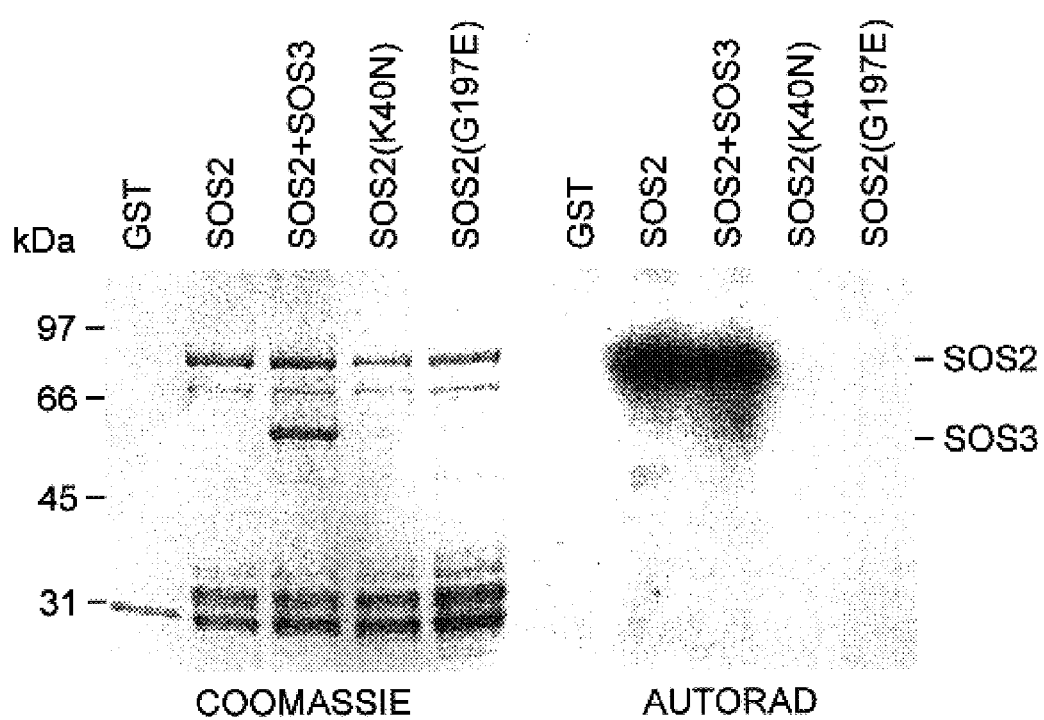
FIG. 4: Autophosphorylation of SOS2 kinase. GST, GST-SOS2, GST-SOS2 plus GST-SOS3, and mutated kinases GST-SOS2 (K40N) and GST-SOS2 (G187E) were expressed in E. coli, purified from bacterial lysates by means of glutathione Sepharose chromatography, incubated with [$\gamma$-$^{32}$p] ATP in kinase buffer, electrophoresed on SDS/polyacrylamide gel, and Coomassie stained (Left), and exposed to x-ray film (Right).

Protein Kinase Activity is Required for SOS2 Function. To determine whether SOS2 encodes a functional protein kinase, the SOS2 ORF was cloned into pGEX-2TK and expressed in bacteria as a C-terminal fusion protein to the bacterial GST. GST-SOS2 was purified from bacterial lysate by affinity chromatography with glutathione-Sepharose beads and shown to have the expected molecular mass of 78 kDa (FIG. 4). Incubation of the recombinant protein with [$\gamma^{32}$P] ATP in an in vitro kinase assay produced a strong phosphorylation signal that is likely the result of SOS2 autophosphorylation (FIG. 4, lanes 2 and 3). Lys-40 of SOS2 corresponds to a highly conserved residue in subdomain II (FIG. 2) that is required for activity in most protein kinases (25). To verify that the phosphorylation signal was because of SOS2 autophosphorylation, Lys-40 was changed to Asn by means of site-directed mutagenesis and the resulting mutant GST-SOS2(K40N) subjected to autophosphorylation assays. The Lys-40 to Asn mutation abolished the autophosphorylation of SOS2 (FIG. 4, lane 4).

In the sos2-5 mutant allele, the highly conserved Gly-197 is changed to Glu. We expressed the sos2-5 allele in bacteria, and the resulting mutant protein GST-SOS2(G197E) was examined for kinase activity. Like the Lys-40Asn mutation, the sos2-5 mutation also abolished the autophosphorylation activity of SOS2 (FIG. 4, lane 5). Because sos2-5 is a recessive mutation (18), the results show that kinase activity is required for SOS2 function in plant salt tolerance.

SOS2 kinase apparently has a very specific substrate requirement because none of the commonly used protein kinase substrates, such as histone H1, myelin basic protein, and casein, was phosphorylated by SOS2 (data not shown). SOS3 was not phosphorylated by SOS2, nor did it appear to affect SOS2 autophosphorylation in vitro (FIG. 4, lane 3). We have recently found several synthetic serine- or threonine-containing peptides that can be readily phosphorylated by SOS2 (30). In addition, phosphorylation of the peptides by SOS2 depended on the presence of both SOS3 and $Ca^{2+}$ (30).

Figure 5A:
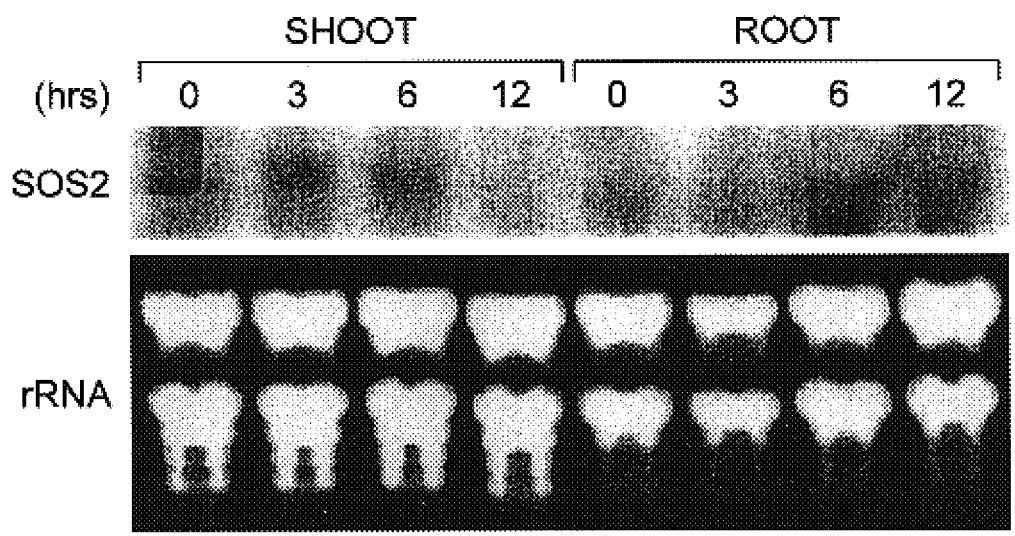
FIG. 5: Regulation of SOS2 expression by salt stress. Plants were treated with 200 mM NaCl (A) or with nutrient solution as a control (B) for the indicated time periods. Total RNA were extracted from roots and shoots, and subjected to Northern blot analysis with $^{32}$P-labeled SOS2 cDNA as probe. Thirty-five micrograms of total RNA was loaded in each lane. Ethidium bromide-stained rRNA bands were used as controls for equal loading.
Figure 5B:
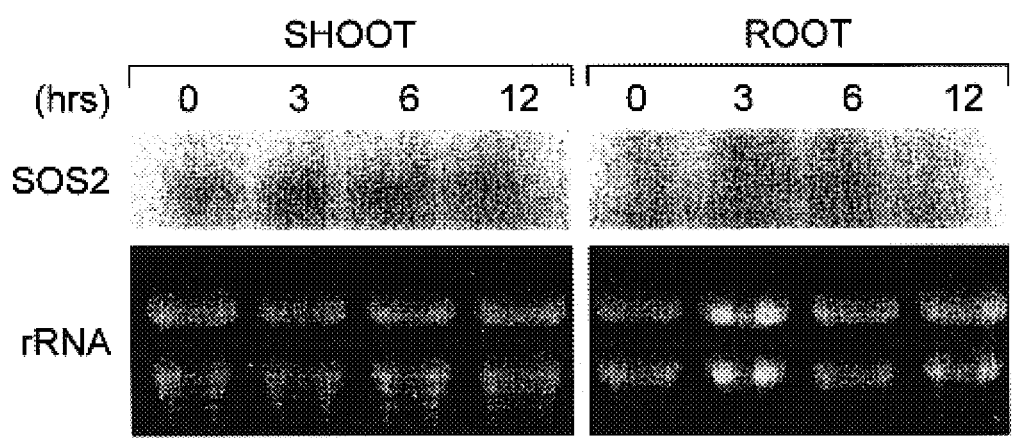

SOS2 Expression in the Root Is Up-Regulated by Salt Stress. To analyze SOS2 expression under salt stress, 10-day-old Arabidopsis seedlings in agar plates were pulled out of agar medium and placed on filter papers soaked with 200 mM NaCl in Murashige and Skoog nutrient solution for 3, 6, or 12 h. Control plants were treated in the same manner, except no NaCl was added to the nutrient solution. After the treatment, roots and shoots were separated at the base of hypocotyls. Total RNA was extracted from control and NaCl-treated tissues. Northern blot analysis using SOS2 cDNA as a probe detected a single transcript of approximately 1.5 kb, the expected size of SOS2 mRNA (FIG. 5). In the root, a very low level of SOS2 mRNA was present in the sample before salt treatment (0 h). After 6 or 12 h of NaCl treatment, increased levels of SOS2 mRNA were detected (FIG. 5A). In the shoot, slight up-regulation of SOS2 transcript was found after 3 or 6 h of NaCl treatment. However, 12 h of NaCl treatment appeared to decrease SOS2 expression in the shoot (FIG. 5A). In the control treatments, only very low levels of SOS2 transcript were detected, and no up-regulation could be seen throughout the time course (FIG. 5B). Overall, the steady-state level of SOS2 transcript was very low, and it took approximately a week of x-ray exposure to obtain the signals shown, whereas a few hours were enough for most other stress-induced genes.

Discussion

SOS2 is a major salt tolerance locus in *A. thaliana* (18). Mutations in the SOS2 gene drastically reduce plant tolerance to high $Na^+$ stress and to low $K^+$ stress. Based on mutant characterization, we have postulated previously that SOS2 might encode a regulatory protein that controls the expression and/or activities of certain K+ and Na+ transporters (18). In the present study, we have isolated the SOS2 gene through positional cloning. Indeed, SOS2 encodes a regulatory protein, a protein kinase. Protein phosphorylation is a frequent theme of cellular signal transduction, and its involvement in plant ion homeostasis and salt tolerance has been hypothesized (31). Our results provide direct evidence that protein phosphorylation is involved in $Na^+$ and $K^+$ homeostasis and plant salt tolerance. Future identification of protein substrate(s) that are phosphorylated by the SOS2 kinase will help understand how plant salt tolerance is regulated by protein phosphorylation. Candidate physiological substrates of SOS2 might include $K^+$ and $Na^+$ transporters and/or transcription factor(s) that control their expression.

The similar phenotypes of sos2 and sos3 mutants suggested that SOS2 and SOS3 may function in the same regulatory pathway (18). We tested and found that SOS3 is not phosphorylated by SOS2, nor did it affect SOS2 autophosphorylation (FIG. 4). Nevertheless, we have discovered that SOS2 physically interacts with SOS3, and SOS2 phosphorylation of peptide substrates is activated by SOS3 in a calcium-dependent manner (30).

SOS2 transcript is present in both roots and shoots. This is consistent with the observation that both the root and the shoot of sos2 mutant plants are hypersensitive to NaCl stress (18). SOS2 expression in the root appears to be up-regulated by NaCl stress. The significance of this up-regulation is unclear. There is certainly a very low level of expression in the root even without stress treatment, which could be detected by very long exposures in the Northern blot analysis or by reverse transcription-PCR (data not shown). The expression of SOS2 in the absence of stress is consistent with its role in primary signal transduction leading to salt adaptation. The slight up-regulation of SOS2 transcript may be important to maintain a sufficient level of SOS2 protein during salt stress. Like SOS2, SOS3 expression level is also very low (J.-K.Z., unpublished results). This probably reflects that SOS3 and SOS2 play regulatory roles that do not necessarily require abundant expression.

SOS2 encodes a protein kinase with a catalytic domain at the N terminus and a regulatory domain at the C terminus. The kinase catalytic domain is essential for SOS2 function. The sos2-5 mutation causes a single amino acid substitution within the catalytic domain that abolishes kinase autophosphorylation, resulting in the loss of SOS2 function and therefore increased sensitivity to salt stress. The regulatory domain also appears to be essential for SOS2 function because mutations that truncate (sos2-2 and sos2-3) or disrupt this domain (sos2-1) render plants hypersensitive to high $Na^+$ and low $K^+$ stresses. The catalytic domain of SOS2 is highly similar to the catalytic domains of SNF1/AMPK kinases (FIG. 3A). SNF1/AMPK kinases function to protect cells against nutritional or environmental stresses that deplete cellular ATP by regulating both metabolism and expression (23, 24). Although the catalytic domain of SO is very similar to those of year SNF1 and mammalian AMPK kinases, SOS2 clearly is not a plant homolog of SNF1/AMPK. This is because true plant SNF1/AMPK kinases, such as SnRK1 share substantial sequence similarity with yeast SNF1 and mammalian AMPK at the C-terminal regulatory domain in addition to very high similarity at the N-terminal catalytic domain (32). Part of the regulatory domain of SOS2 is similar to the DNA repair and replication checkpoint kinase CHK1 (FIG. 3B) which is required for cell cycle arrest in response to DNA damage (27–29). The sequence similarity with CHK1 kinase is interesting because sos2 mutants show cell cycle defect at the root meristem in the presence of Na⁺ stress (J.-K.Z., unpublished data).

Although several protein kinases were previously reported to play roles in plant stress responses, none of them functions in ion homeostasis (33–36). The AtDBF2 protein kinase was identified by its ability to increase not only salt tolerance but also osmotic heat and cold stress tolerance when overexpressed in *Saccharomyces cerevisiae* or in cultured tobacco cells (33). The mitogen activated protein kinase MKK4 from alfalfa was shown to be activated by cold and drought but not by salt stress (34). Extopic expression of a calcium-dependent protein kinase in maize protoplasts activates the expression of cold- and abscisic responsive genes (36). The transcript levels of several protein kinases were shown to be up-regulated by various stresses including touch, cold, and osmotic stress (35); however, functions remain unknown. In contrast to these previously reported protein kinases that are involved in either general responses or in osmotic and cold stress responses, the SOS2 kinase has specific roles in plant adaptation to high Na⁺ and K⁺ stresses (18).

Obviously, numerous modifications and variations of the present invention are possible in light of the above teachings. It is therefore to be understood that within the scope of the appended claims, the invention may be practiced otherwise than as specifically described herein.

REFERENCES

1. Sze, H., Li, X. & Palmgren, M. G. (1999) *Plant Cell* 11, 677–689.
2. Sentenac, H., BVonnenud, N., Minet, M., Lacroute, F., Salmonm, J. M., Gay-nard, F. & Grignon, C. (1992) *Science* 256, 663–665.
3. Hirsch, R. E., Lewis, B. D., Spadling, E. P. & Sussman, M. R. (1998) *Science* 280, 918–921.
4. Anderson, J. A., Huprikar, S. S., Kochian, L. V., Lucas, W. J. & Gaber, R. F. (1992) *Proc. Natl. Acad. Sci. USA* 89, 3736–3740.
5. Nakamura, R. L., Mckendree, W. L., Jr., Hirsch, R. E., Sedbrook, J. C., Gaber, R. & Sussman, M. R. (1995) *Plant Physiol.* 109, 371–374.
6. Gaymard, F., Pilot, G. Lacombe, B., Bouchez, D., Bruneau, D., Boucherez, J., Michaux-Ferriere, N., Thibaud, J. B. & Sentenac, H. (1998) *Cell* 94, 647–655.
7. Rubio, F., Gassmann, W. & Schroeder, J. I. (1995) *Science* 270, 1660–1663.
8. Kim, E. J., Kwak, J. M., Uozumi, N. & Schoreder, J. I. (1998) *Plant Cell* 10, 61–62.
9. Fu, H.-H. & Lunn, S. (1998) *Plant Cell* 10, 63–73.
10. Schroeder, J. I., Ward, J. M. & Gassmann, W. (1994) *Annu. Rev. Biophys. Biomol. Struct.* 23, 441–471.
11. Gaxiola, R. A., Rao, R., Sherman, A., Grisafi P., Alper. Sl. L. & Fink, G. R. (1999) *Proc. Natl. Acad. Sci. USA* 96, 1480–1485.
12. Apse, M. P. Aharon, G. S., Soedden, W. A. & Blumwald, E. (1999) *Science* 285, 1256–1258.
13. Rea, P. A. & Poole, R. J. (1993) *Annu. Rev. Plant Physiol. Plant Biol.* 44, 157–180.
14. Epstein, E., Norlyn, J. D., Rush, D. W., Kingsbury, R. W., Kelley, D. B., Cunningham, G. A. & Wronn, A. F. (1980) *Science* 210, 399–404.
15. Wu, S. U., Ding, L. & Zhu, J. K. (1996) *Plant Cell* 8, 617–627.
16. Murguia, J. R., Belles, J. M. & Serrano, R. (1995) *Science* 267, 232–234.
17. Liu, J. & Zhu, J. K. (1997) *Proc. Natl. Acad. Sci. USA* 94, 14960–14964.
18. Zhu, J.-K., Liu, J. & Xiong, L. (1998) *Plant Cell* 10, 1181–1192.
19. Liu, J. & Zhu, J.-K. (1998) *Science* 280, 1943–1945.
20. Nakamura, T. Y., Liu, Y., Hirara, D., Namba, H., Harada, S., Hirokawa, Miyakawa, T. (1993) *EMBO J.* 12, 4063–4071.
21. Mendoza, I., Rubio, F., Rodriguez-Navarro, A., & Pardo, J. M. (1994) *J Biol Chem.* 269, 8792–8796.
22. Ishitani, M., Xiong, L., Stevenson, B. & Zhu, J.-K (1997) *Plant Cell* 1935–1949.
23. Celenza, J. L. & Carlson, M. (1986) *Science* 233, 1175–1180.
24. Mitchelhill, K. L. Stapleton, D., Gao, G., House, C. Mitchell, B., Ks. Witters, L. A. & Kemp, B. E., (1994) *J Biol Chem.* 269, 2361–2364.
25. Hanks, S. K., Quinn, A. M. & Hunter, T. (1988) *Science* 241, 42–52.
26. Hanks, S. K. & Hunter, T., (1995) in *The Protein Kinase Facts Book*, eds. D. & Hanks, S. (Academic, London), Vol. 1, pp. 7–47.
27. Walworth, N., Davey, S. & Beach, D. (1993) *Nature* (London) 363, 368–371.
28. Walworth, N. C. & Bernards, R. (1996) *Science* 271, 353–356.
29. Boddy, M. N., Furnari, B., Moadesert, O. & Russell, P. (1998) *Science* 280: 909–912.
30. Halfter, U., Ishitani, M. & Zhu, J.-K. (2000) *Proc. Natl. Acad. Sci. USA.* 97(7):3735–40.
31. Niu, X., Bressan, R. A., Hasegawa, P. M. & Pardo, J. M. (1995) *Plant Physiol* 109, 735–742.
32. Halford, N. G. & Hardle, D. G. (1998) *Plant Mol. Biol.* 27, 735–748.
33. Lee, J. H., Van Moningu, M. & Verbruggen, N. (1999) *Proc. Natl. Acad Sci* USA 96, 5873–5877.
34. Jonnk, C., Kiegerl, S., Lighterink, W., Barker, P. J., Huskisson, N. S. H. (1996) *Proc. Natl. Acad. Sci.* USA 93, 11274–11279.
35. Mizoguchi, T., Irie, K., Hirayama, T., Hayashida, N., Yamaguchi-Shino, Matsumoto, K. & Shinozaki, K. (1996) *Proc. Natl. Acad. Sci.* USA 93:765–769.
36. Sheen, J. (1996) *Science* 274, 1900–1902.

In the claims:

1. An isolated polynucleotide comprising a nucleic acid sequence consisting of SEQ ID NO:1.
2. The isolated polynucleotide of claim 1, wherein said nucleic acid sequence is operably linked to a heterologous promoter.
3. The isolated polynucleotide of claim 2, wherein said heterologous promoter is an inducible promoter.
4. An isolated polynucleotide which is fully complementary the polynucleotide of claim 1.
5. A vector comprising the isolated polynucleotide of claim 1.
6. A host cell comprising the isolated polynucleotide of claim 1.
7. A plant cell comprising the isolated polynucleotide of claim 1.
8. A transgenic plant comprising the isolated polynucleotide of claim 1.
9. The transgenic plant of claim 8, wherein said plant is *Arabidopsis thaliana*.
10. The transgenic plant of claim 8, wherein said plant is selected from the group consisting of wheat, corn, peanut, cotton, oat, and soybean plant.
11. A method of making a transgenic plant comprising introducing the polynucleotide of claim 1 into the plant.
12. An isolated polynucleotide comprising a nucleic acid sequence consisting of a sequence encoding SEQ ID NO:2.
13. The isolated polynucleotide of claim 12, wherein said nucleic acid sequence is operably linked to a heterologous promoter.
14. The isolated polynucleotide of claim 13, wherein said heterologous promoter is an inducible promoter.
15. An isolated polynucleotide which is fully complementary to the polynucleotide of claim 12.
16. A vector comprising the isolated polynucleotide of claim 12.
17. A host cell comprising the isolated polynucleotide of claim 12.
18. A plant cell comprising the isolated polynucleotide of claim 12.
19. A transgenic plant comprising the isolated polynucleotide of claim 12.
20. The transgenic plant of claim 19, wherein said plant is *Arabidopsis thaliana*.
21. The transgenic plant of claim 19, wherein said plant is selected from the group consisting of wheat, corn, peanut, cotton, oat, and soybean plant.
22. A method of making a transgenic plant comprising introducing the polynucleotide of claim 12 into the plant.
23. An isolated polynucleotide consisting of SEQ ID NO:1.
24. An isolated polynucleotide comprising the polynucleotide of claim 23 operably linked to a heterologous promoter.
25. The isolated polynucleotide of claim 24, wherein said heterologous promoter is an inducible promoter.
26. An isolated polynucleotide which is fully complementary to the polynucleotide of claim 23.
27. A vector comprising the isolated polynucleotide of claim 23.
28. A host cell comprising the isolated polynucleotide of claim 23.
29. A plant cell comprising the isolated polynucleotide of claim 23.
30. A transgenic plant comprising the isolated polynucleotide of claim 23.
31. The transgenic plant of claim 30, wherein said plant Arabidopsis thaliana.
32. The transgenic plant of claim 30, wherein said plant is selected from the group consisting of wheat, corn, peanut, cotton, oat, and soybean plant.
33. A method of making a transgenic plant comprising introducing the polynucleotide of claim 23 into the plant.
34. An isolated polynucleotide consisting of a nucleic acid sequence encoding SEQ ID NO:2.
35. The isolated polynucleotide of claim 34, wherein said nucleic acid sequence is operably linked to a heterologous promoter.
36. The isolated polynucleotide of claim 35, wherein said heterologous promoter is an inducible promoter.
37. An isolated polynucleotide which is fully complementary the polynucleotide of claim 34.
38. A vector comprising the isolated polynucleotide of claim 34.
39. A host cell comprising the isolated polynucleotide of claim 34.
40. A plant cell comprising the isolated polynucleotide of claim 34.
41. A transgenic plant comprising the isolated polynucleotide of claim 34.
42. The transgenic plant of claim 41, wherein said plant is *Arabidopsis thaliana*.
43. The transgenic plant of claim 41, wherein said plant is selected from the group consisting of wheat, corn, peanut, cotton, oat, and soybean plant.
44. A method of making a transgenic plant comprising introducing the polynucleotide of claim 34 into the plant.
45. An isolated polynucleotide comprising a nucleic acid sequence consisting of a sequence encoding a polypeptide having 95% sequence identity with SEQ ID NO:2, wherein said polypeptide has serine/threonine kinase activity.
46. The isolated polynucleotide of claim 45, wherein said nucleic acid sequence is operably linked to a heterologous promoter.
47. The isolated polynucleotide of claim 46, wherein said heterologous promoter is an inducible promoter.
48. An isolated polynucleotide which is fully complementary to the polynucleotide of claim 45.
49. A vector comprising the isolated polynucleotide of claim 45.
50. A host cell comprising the isolated polynucleotide of claim 45.
51. A plant cell comprising the isolated polynucleotide of claim 45.
52. A transgenic plant comprising the isolated polynucleotide of claim 45.

53. The transgenic plant of claim 52, wherein said plant is *Arabidopsis thaliana*.

54. The transgenic plant of claim 52, wherein said plant is selected from the group consisting of wheat, corn, peanut, cotton, oat, and soybean plant.

55. A method of making a transgenic plant comprising introducing the polynucleotide of claim 45, into the plant.

56. An isolated polynucleotide consisting of a nucleic acid sequence encoding a polypeptide having 95% sequence identity with SEQ ID NO:2, wherein said polypeptide has serine/threonine kinase activity.

57. The isolated polynucleotide of claim 56, wherein said nucleic acid sequence is operably linked to a heterologous promoter.

58. The isolated polynucleotide of claim 57, wherein said heterologous promoter is an inducible promoter.

59. An isolated polynucleotide which is fully complementary to the polynucleotide of claim 56.

60. A vector comprising the isolated polynucleotide of claim 56.

61. A host cell comprising the isolated polynucleotide of claim 56.

62. A plant cell comprising the isolated polynucleotide of claim 56.

63. A transgenic plant comprising the isolated polynucleotide of claim 56.

64. The transgenic plant of claim 63, wherein said plant is *Arabidopsis thaliana*.

65. The transgenic plant of claim 63, wherein said plant is selected from the group consisting of wheat, corn, peanut, cotton, oat, and soybean plant.

66. A method of making a transgenic plant comprising introducing the polynucleotide of claim 56 into the plant.

* * * * *

UNITED STATES PATENT AND TRADEMARK OFFICE
CERTIFICATE OF CORRECTION

PATENT NO.   : 6,784,343 B2
DATED        : August 31, 2004
INVENTOR(S)  : Zhu et al.

It is certified that error appears in the above-identified patent and that said Letters Patent is hereby corrected as shown below:

<u>Title page,</u>
Item [75], Inventors, should read:
-- [75]  Inventors:  Jian-Kang Zhu, Tuscon, AZ (US); Jiping Liu, Ithaca, NY (US); Manabu Ishitani, Cary, NC (US); Cheol-Soo Kim, Tuscon, AZ (US); Ursula Halfter, Tuscon, AZ (US) --

Signed and Sealed this

Thirtieth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,784,343 B2  
APPLICATION NO. : 09/824735  
DATED : August 31, 2004  
INVENTOR(S) : Zhu et al.

It is certified that error appears in the above-identified patent and that said Letters Patent is hereby corrected as shown below:

On the title page, Item (75), the Inventor's information is incorrect. Item (75) should read:

-- (75) Inventors: Jian-Kang Zhu, Tucson, AZ (US); Jiping Liu, Ithaca, NY (US); Manabu Ishitani, Cary, NC (US); Cheol-Soo Kim, Tucson, AZ (US); Ursula Halfter, Tucson, AZ (US) --

Signed and Sealed this

Fourteenth Day of November, 2006

JON W. DUDAS  
*Director of the United States Patent and Trademark Office*